(12) United States Patent
Combs et al.

(10) Patent No.: US 9,290,514 B2
(45) Date of Patent: Mar. 22, 2016

(54) TRICYCLIC HETEROCYCLES AS BET PROTEIN INHIBITORS

(71) Applicants: Incyte Corporation, Wilmington, DE (US); Incyte Holdings Corporation, Wilmington, DE (US)

(72) Inventors: Andrew P. Combs, Kennett Square, PA (US); Eddy W. Yue, Landenberg, PA (US); Richard B. Sparks, Wilmington, DE (US); Thomas P. Maduskuie, Jr., Wilmington, DE (US)

(73) Assignees: Incyte Holdings Corporation, Wilmington, DE (US); Incyte Corporation, Wilmington, DE (US)

( * ) Notice: Subject to any disclaimer, the term of this patent is extended or adjusted under 35 U.S.C. 154(b) by 0 days.

(21) Appl. No.: 14/324,560

(22) Filed: Jul. 7, 2014

(65) Prior Publication Data
US 2015/0011540 A1    Jan. 8, 2015

Related U.S. Application Data

(60) Provisional application No. 61/843,638, filed on Jul. 8, 2013.

(51) Int. Cl.
C07D 498/04 (2006.01)
C07D 498/06 (2006.01)

(52) U.S. Cl.
CPC .................................. C07D 498/06 (2013.01)

(58) Field of Classification Search
CPC ............................ C07D 498/04; C07D 498/06
USPC ...................................... 544/101; 514/230.2
See application file for complete search history.

(56) References Cited

U.S. PATENT DOCUMENTS

| 5,589,476 | A | 12/1996 | Jegham et al. |
| 2007/0191447 | A1 | 8/2007 | Kodo et al. |
| 2013/0261109 | A1 | 10/2013 | Miyoshi et al. |
| 2013/0281396 | A1 | 10/2013 | McLure et al. |
| 2013/0281397 | A1 | 10/2013 | McLure et al. |
| 2013/0281398 | A1 | 10/2013 | McLure et al. |
| 2013/0281399 | A1 | 10/2013 | McLure et al. |
| 2014/0135316 | A1 | 5/2014 | Albrecht et al. |
| 2014/0275030 | A1 | 9/2014 | Combs et al. |
| 2015/0148342 | A1 | 5/2015 | Yue et al. |
| 2015/0148372 | A1 | 5/2015 | Yue et al. |
| 2015/0148375 | A1 | 5/2015 | Yue et al. |
| 2015/0175604 | A1 | 6/2015 | Rodgers et al. |

FOREIGN PATENT DOCUMENTS

| CA | 2171579 | 9/1996 |
| EP | 0 732 334 | 9/1996 |
| EP | 1462103 | 9/2004 |
| EP | 2 239 264 | 10/2010 |
| FR | 2747678 | 10/1997 |
| JP | 2013/010719 | 1/2013 |
| WO | WO 02/00196 | 1/2002 |
| WO | WO 2004/024736 | 3/2004 |
| WO | WO 2007/018998 | 2/2007 |
| WO | WO 2009/020559 | 2/2009 |
| WO | WO 2009/020677 | 2/2009 |
| WO | WO 2009/084693 | 7/2009 |
| WO | WO 2010/046190 | 4/2010 |
| WO | WO 2010/144679 | 12/2010 |
| WO | WO 2010/144680 | 12/2010 |
| WO | WO 2011/054553 | 5/2011 |
| WO | WO 2011/054841 | 5/2011 |
| WO | WO 2011/054843 | 5/2011 |
| WO | WO 2011/054844 | 5/2011 |
| WO | WO 2011/054845 | 5/2011 |
| WO | WO 2011/054846 | 5/2011 |
| WO | WO 2011/054848 | 5/2011 |
| WO | WO 2011/054851 | 5/2011 |
| WO | WO 2011/143651 | 11/2011 |
| WO | WO 2011/143657 | 11/2011 |
| WO | WO 2011/143660 | 11/2011 |
| WO | WO 2011/143669 | 11/2011 |
| WO | WO 2011/161031 | 12/2011 |
| WO | WO 2012/075383 | 6/2012 |
| WO | WO 2012/075456 | 6/2012 |
| WO | WO 2012/116170 | 8/2012 |

(Continued)

OTHER PUBLICATIONS

Ai et al., "Signal-induced Brd4 release from chromatin is essential for its role transition from chromatin targeting to transcriptional regulation," Nucleic Acids Res., 2011, 1-13.
Bamborough et al., "Fragment-Based Discovery of Bromodomain Inhibitors Part 2: Optimization of Phenylisoxazole Sulfonamides," J Med Chem., 2012, 55:587-596.
Bartholomeeusen et al., "BET bromodomain inhibition activates transcription via a transient release of P-TEFb from 7SK snRNP," JBC, 2012, 16 pages.
Belkina and Denis, " BET domain co-regulators in obesity inflammation and cancer," Nat Rev Cancer, Jul. 2012, 12:465-477.
Chiang, "Brd4 engagement from chromatin targeting to transcriptional regulation: selective contact with acetylated histone H3 and H4," Biology Reports, Dec. 2009, 1:98, 7 pages.

(Continued)

*Primary Examiner* — Kahsay Habte
(74) *Attorney, Agent, or Firm* — Fish & Richardson P.C.

(57) ABSTRACT

The present invention relates to tricyclic heterocycles of Formula (I), which are inhibitors of BET proteins such as BRD2, BRD3, BRD4, and BRD-t and are useful in the treatment of diseases such as cancer.

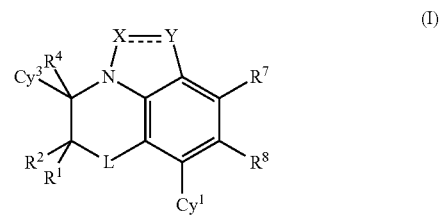

44 Claims, No Drawings

(56) References Cited

FOREIGN PATENT DOCUMENTS

| | | |
|---|---|---|
| WO | WO 2012/143413 | 10/2012 |
| WO | WO 2012/143415 | 10/2012 |
| WO | WO 2012/143416 | 10/2012 |
| WO | WO 2012/150234 | 11/2012 |
| WO | WO 2012/151512 | 11/2012 |
| WO | WO 2012/174487 | 12/2012 |
| WO | WO 2012/178208 | 12/2012 |
| WO | WO 2013/019710 | 2/2013 |
| WO | WO 2013/024104 | 2/2013 |
| WO | WO 2013/027168 | 2/2013 |
| WO | WO 2013/029548 | 3/2013 |
| WO | WO 2013/030150 | 3/2013 |
| WO | WO 2013/033268 | 3/2013 |
| WO | WO 2013/033269 | 3/2013 |
| WO | WO 2013/033270 | 3/2013 |
| WO | WO 2013/043553 | 3/2013 |
| WO | WO 2013/044511 | 4/2013 |
| WO | WO 2013/064900 | 5/2013 |
| WO | WO 2013/097052 | 7/2013 |
| WO | WO 2013/097601 | 7/2013 |
| WO | WO 2013/148197 | 10/2013 |
| WO | WO 2013/155695 | 10/2013 |
| WO | WO 2013/156869 | 10/2013 |
| WO | WO 2013/158952 | 10/2013 |
| WO | WO 2013/175281 | 11/2013 |
| WO | WO 2013/184876 | 12/2013 |
| WO | WO 2013/184878 | 12/2013 |
| WO | WO 2013/185284 | 12/2013 |
| WO | WO 2013/186612 | 12/2013 |
| WO | WO 2013/188381 | 12/2013 |
| WO | WO 2014/001356 | 1/2014 |
| WO | WO 2014/015175 | 1/2014 |
| WO | WO 2014/026997 | 2/2014 |
| WO | WO 2014/028547 | 2/2014 |
| WO | WO 2014/048945 | 4/2014 |
| WO | WO 2014/068402 | 5/2014 |
| WO | WO 2014/076146 | 5/2014 |
| WO | WO 2014/078257 | 5/2014 |
| WO | WO 2014/080290 | 5/2014 |
| WO | WO 2014/080291 | 5/2014 |
| WO | WO 2014/095774 | 6/2014 |
| WO | WO 2014/095775 | 6/2014 |
| WO | WO 2014/096965 | 6/2014 |
| WO | WO 2014/128655 | 8/2014 |
| WO | WO 2014/134232 | 9/2014 |
| WO | WO 2014/134267 | 9/2014 |
| WO | WO 2014/139324 | 9/2014 |
| WO | WO 2014/140076 | 9/2014 |
| WO | WO 2014/140077 | 9/2014 |
| WO | WO 2014/143768 | 9/2014 |
| WO | WO 2014/145051 | 9/2014 |
| WO | WO 2014/152029 | 9/2014 |
| WO | WO 2014/154760 | 10/2014 |
| WO | WO 2014/154762 | 10/2014 |
| WO | WO 2014/159392 | 10/2014 |
| WO | WO 2014/159837 | 10/2014 |
| WO | WO 2014/160873 | 10/2014 |
| WO | WO 2014/164596 | 10/2014 |
| WO | WO 2014/164771 | 10/2014 |
| WO | WO 2014/164780 | 10/2014 |
| WO | WO 2014/165127 | 10/2014 |
| WO | WO 2014/165143 | 10/2014 |
| WO | WO 2014/170350 | 10/2014 |
| WO | WO 2014/173241 | 10/2014 |
| WO | WO 2014/182929 | 11/2014 |
| WO | WO 2014/191894 | 12/2014 |
| WO | WO 2014/191896 | 12/2014 |
| WO | WO 2014/191906 | 12/2014 |
| WO | WO 2014/191911 | 12/2014 |
| WO | WO 2014/202578 | 12/2014 |
| WO | WO 2014/206345 | 12/2014 |
| WO | WO 2014/210425 | 12/2014 |
| WO | 2015013635 | 1/2015 |
| WO | WO 2015/002754 | 1/2015 |
| WO | WO 2015/004533 | 1/2015 |
| WO | WO 2015/004534 | 1/2015 |

OTHER PUBLICATIONS

Chung et al., "Discovery and Characterization of Small Molecule Inhibitors of the BET Family Bromodomains," J Med Chem., 2011, 54:3827-3838.

Chung et al., "Fragment-Based Discovery of Bromodomain Inhibitors Part 1. Inhibitor Binding Modes and Implications for Lead Discovery," J Med Chem., 2011, 11 pages.

Chung et al., "Fragment-based discovery of bromodomain inhibitors part 1: inhibitor binding modes and implications for lead discovery," Supporting Information, 2011, 6 pages.

Dawson et al , "Inhibition of BET recruitment to chromatin as an effective treatment for MLL-fusion leukaemia," Nature, 2011, 5 pages.

Dawson, "Supplementary Information. Inhibition of BET recruitment to chromatin as an effective treatment for MLL-fusion leukaemia," Nature, 2011, 50 pages.

Delmore et al., "BET bromodomain inhibition as a therapeutic strategy to target c-Myc," Cell, 2011, 146(6):904-917, Supplemental Information: S1-S11.

Draker et al., "A Combination of H2A.Z and H4 Acetylation Recruits Brd2 to Chromatin during Transcriptional Activation," PLoS Genet., Nov. 2012, 8(11):e1003047, 17 pages.

Dorwald, F. Zaragoza. Side Reactions in Organic Synthesis: A Guide to Successful Synthesis Design, Weinheim: Wiley-VCH Verlag GmbH & Co. KGaA, 2005, Preface, 2 pages.

Filippakopoulos and Knapp, "Targeting bromodomains: epigenetic readers of lysine acetylation," Nature Rev Drug Disc., May 2014, 13:337-356.

Filippakopoulos et al., "Benzodiazepines and benzotriazepines as protein interaction inhibitors targeting bromodomains of the BET family," Bioorg Med Chem., 2011, 9 pages.

Filippakopoulos et al., "Histone Recognition and Large-Scale Structural Analysis of the Human Bromodomain Family," Cell, Mar. 2012, 149:214-231.

Filippakopoulos et al., "Supplemental Information: Selective inhibition of BET bromodomains," Nature, 2010, 468:1067-1073.

Floyd et al., "Supplemental Information: The bromodomain protein Brd4 insulates chromatin from DNA damage signalling," Nature, 2013, 14 pages.

Floyd et al., "The bromodomain protein Brd4 insulates chromatin from DNA damage signalling," Nature, 2013, 498:246-250.

French et al., "BRD—NUT oncoproteins: a family of closely related nuclear proteins that block epithelial differentiation and maintain the growth of carcinoma cells," Oncogene, 2008, 27:2237-2242.

French, "Demystified molecular pathology of NUT midline carcinomas," J Clin Pathol., 2010, 63:492-496.

French, "NUT midline carcinoma," Cancer Genet Cytogenetics, 2010, 203:16-20.

Frizzo et al., "Structural and thermodynamic properties of new pyrazolo[3,4-d] pyridazinones," Thermochimica Acta., Oct. 2013, 574:63-72.

Hewings et al., "3,5-Dimethylisoxazoles Act As Acetyl-lysine-mimetic Bromodomain Ligands," J Med Chem., 2011, 54:6761-6770.

Hewings et al., "Progress in the Development and Applciation of Small Molecule Inhibitors of Bromodomain-Acetyl-lysine Interactions," J Med Chem., Nov. 2012, 104 pages (Author Manuscript).

Houzelstein et al., "Growth and Early Postimplantation Defects in Mice Deficient for the Bromodomain-Containing Protein Brd4," Mole Cell Biol., Jun. 2002, 22(11):3794-3802.

International Search Report and Written Opinion in International Application No. PCT/US2014/067598, mailed Feb. 13, 2015, 9 pages.

International Search Report and Written Opinion in International Application No. PCT/US2014/067629, mailed Feb. 16, 2015, 11 pages.

International Search Report and Written Opinion in International Application No. PCT/US2014/067691, mailed Feb. 2, 2015, 10 pages.

(56) References Cited

OTHER PUBLICATIONS

Jin et al., "c-Myb binds MLL through menin in human leukemia cells and is an important driver of MLL-associated leukemogenesis," J Clinc Invest., 2010, 120(2):593-606.
Jordan, "Tamoxifen: A Most Unlikely Pioneering Medicine," Nature Reviews: Drug Discovery, 2003, 205.
Jung et al., "Affinity Map of BRD4 Interactions with the Histone H4 Tail and the Small Molecule Inhibitor JQ1," J Biol Chem., 2014, 28 pages.
Lockwood et al., "Sensitivity of human lung adenocarcinoma cell lines to targeted inhibition of BET epigenetic signaling proteins," PNAS Early Edition, 2012, 14 pages.
Martin et al., "Cyclin-Dependent Kinase Inhibitor Dinaciclib Interacts with the Acetyl-Lysine Recognition Site of Bromodomains," ACS Chem Biol., 2013, 8:2360-2365.
Maruyama et al., "A Mammalian Bromodomain Protein, Brd4, Interacts with Replication Factor C and Inhibits Progression to S Phase," Mol Cell Biol., 2002, 22(18):6509-6520.
Matzuk et al., "Small-Molecule Inhibition of BRDT for Male Contraception," Cell, Aug. 2012, 150:673-684.
McLure et al., "RVX-208, an Inducer of ApoA-I in Humans, Is a BET Bromodomain Antagonist," Plos One, Dec. 2013, 8(12):e83190, 12 pages.
Mertz et al., "Targeting MYC dependence in cancer by inhibiting BET bromodomains," PNAS, 2011, 108(40):16669-16674.
Mirguet et al., "From ApoA1 upregulation to BET family bromodomain inhibition: Discovery of I-BET151," Bioorg Med Chem Lett., 2012, 22:2963-2967.
Moriniere et al., "Cooperative binding of two acetylation marks on a histone tail by a single bromodomain," Nature, 2009, 461:664-669.
Muller et al., "Bromodomains as therapeutic targets," Expert Reviews, 2011, 13:e29, 21 pages.
Nicodeme et al., "Supplementary Information: Suppression of inflammation by a synthetic histone mimic," Nature, 2010, 40 pages.
Nicodeme et al., "Suppression of inflammation by a synthetic histone mimic," Nature, 2010, 468:1119-1123.
Nishiyama et al., "Brd4 Is Required for Recovery from Antimicrotubule Drug-induced Mitotic Arrest: Preservation of Acetylated Chromatin," Mol Biol Cell, Feb. 2006, 17:814-823.
Ott et al., "BET bromodomain inhibition targets both c-Myc and IL7R in high-risk acute lymphoblastic leukemia," Blood, published online 2012, 29 pages.
Picaud et al., "RVX-208, an inhibitor of BET transcriptional regulators with selectivity for the second bromodomain," PNAS Early Edition, 2013, 6 pages.
Picaud et al., "Supplemental Information: RVX-208, an inhibitor of BET transcriptional regulators with selectivity for the second bromodomain," PNAS Early Edition, 2013, 9 pages.
Prinjhas et al., "Place your BETs: the therapeutic potential of bromodomains," Trends Pharmacol Sci., 2012, 33(3):146-153.
Rahman et al., "The Brd4 Extraterminal Domain Confers Transcription Activation Independent of pTEFb by Recruiting Multiple Proteins, Including NSD3," Mol Cell Biol., Jul. 2011, 31(13):2641-2652.
Sanchez and Zhou, "The role of human bromodomains in chromatin biology and gene transcription," Curr Opin Drug Discov Devel., Sep. 2009, 12(5):659-665 (Author Manuscript).
Schroder et al., "Two-pronged Binding with Bromodomain-containing Protein 4 Liberates Positive Transcription Elongation Factor b from Inactive Ribonucleoprotein Complexes," J Biol Chem., Jan. 6, 2012, 287(2):1090-1099.
Schwartz et al., "Differentiation of NUT Midline Carcinoma by Epigenomic Reprogramming," Cancer Res., 2011, 71:2686-2696.
Seal et al., "Identification of a novel series of BET family bromodomain inhibitors: Binding mode and profile of I-BET151 (GSK1210151A)," Bioorg Med Chem., 2012, 22:2968-2972.
Smith et al., "Genome-wide siRNA screen identifies SMCX, EP400, and Brd4 as E2-dependent regulators of human papillomavirus oncogene expression," PNAS, Feb. 23, 2010, 107(8):3752-3757.
Stenman et al., "New tricks from an old oncogene: Gene fusion and copy number alterations of MYB in human cancer," Cell Cyle, Aug. 2010, 9(15):2986-2955.
Vidler et al., "Druggability Analysis and Structural Classification of Bromodomain Acetyl-lysine Binding Sites," J Med Chem., 2012, 14 pages.
Wang et al., "The Bromodomain Protein Brd4 Associated with Acetylated Chromatin is Important for Maintenance of Higher-Order Chromatin Structure," JBC, 2012, 22 pages.
Weidner-Glunde et al., "What do viruses BET on?" Frontiers Biosci., Jan. 2010, 15:537-549.
Wu and Chiang et al., "The Double Bromodomaincontaining Chromatin Adaptor Brd4 and Transcriptional Regulation," J Biol Chem., May 2007, 282(18):13141-13145.
Wu et al., "Brd4 links chromatin targeting to HPV transcriptional silencing," Genes Dev., 2006, 20:2383-2396.
Yan et al., "Perturbation of BRD4 Protein Function by BRD4-NUT Protein Abrogates Cellular Differentiation in NUT Midline Carcinoma," J Biol Chem., Aug. 2011, 286(31):27663-27675.
Yan et al., "Supplemental Data: Perturbation of BRD4 Protein Function by BRD4-NUT Protein Abrogates Cellular Differentiation in NUT Midline Carcinoma," J Biol Chem., Aug. 2011, 12 pages.
Yang et al., "Brd4 Recruits P-TEFb to Chromosomes at Late Mitosis to Promote G1 Gene Expression and Cell Cycle Progression," Mol Cell Biol., Feb. 2008, 28(3):967-976.
You et al., "Regulation of Aurora B Expression by the Bromodomain Protein Brd4," Mol Cell Biol., Sep. 2009, 29(18):5094-5103.
Zhang et al., "Bromodomain-Containing-Protein 4 (BRD4) Regulates RNA Polymerase II Serine 2 Phosphorylation in Human CD4+ T Cells," JBC, 2012, 30 pages.
Zuber et al., "An integrated approach to dissecting oncogene addiction implicates a Myb-coordinated self-renewal program as essential for leukemia maintenance," Genes Dev., 2011, 25:1628-1640.
Zuber et al., "Supplemental Information: RNAi screen identifies Brd4 as a therapeutic target in acute myeloid leukaemia," Nature, 2011, 33 pages.
International Search Report and Written Opinion in International Application No. PCT/US2014/027872, mailed Jun. 30, 2014, 12 pages.
Belkina et al., "BET Protein Function is Required for Inflammation: Brd2 Genetic Disruption and BET Inhibitor JQ1 Impair Mouse Macrophage Inflammatory Responses," J Immunol., 2013, 190:3670-3678.
Berge et al., "Pharmaceutical Salts," J Pharm. Sci., 1977, 66(1):1-19.
Blom et al., "Optimizing Preparative LC-MS Configurations and Methods for Parallel Synthesis Purification," J Comb Chem., 2003, 5(5):670-683.
Blom et al., "Preparative LCMS Purification: Improved Compound Specific Method Optimization," J Comb Chem., 2004, 6(6):874-883.
Blom, "Two-pump at-column-dilution configuration for preparative liquid chromatography-mass spectrometry," J Comb Chem., 2002, 4(4):295-301.
Delmore et al., "BET bromodomain inhibition as a therapeutic strategy to target c-Myc," Cell, 2011, 146(6):904-917.
Devaiah et al., "BRD4 is an atypical kinase that phosphorylates serine2 of the RNA polymerase II carboxy-terminal domain," Proc. Nat. Acad. Sci. USA., 2012, 109(18):6927-6932.
Filippakopoulos et al., "Selective inhibition of BET bromodomains," Nature, 2010, 468:1067-1073.
French et al., "BRD4-NUT fusion oncogene: a novel mechanism in aggressive carcinoma," Cancer Res., 2003, 63(2):304-307.
French et al., "Midline carcinoma of children and young adults with NUT rearrangement," J Clin. Oneal., 2004, 22(20):4135-4139.
Gallenkamp et al., "Bromodomains and their Pharmacological Inhibitors," Chem Med Chem., Mar. 2014, 9(3):438-464.
Gamier et al., "BET bromodoma in inhibitors: a patent review," Exp Opin Therapeutic Patents, Feb. 2014, 24(2):185-199.
Hewings et al., "Progress in the Development and Applciation of Small Molecule Inhibitors of Bromodomain-Acetyl-lysine Interactions," J Med Chem., Nov. 2012, 55(22):9393-9413.
Huang et al., "Brd4 coactivates transcriptional activation of NF-κB via specific binding to acetylated Re1A," Mol. Cell Biol., 2009, 29(5):1375-1387.

(56) References Cited

OTHER PUBLICATIONS

Jang et al., "The bromodomain protein Brd4 is a positive regulatory component of P-TEFb and stimulates RNA polymerase II-dependent transcription," Mol. Cell, 2005, 19(4):523-534.

Lamonica et al., "Bromodomain protein Brd3 associates with acetylated GATA1 to promote its chromatin occupancy at erythroid target genes," Proc. Nat. Acad. Sci., USA, 2011, 108(22):E159-168.

Leroy et al., "The double bromodomain proteins Brd2 and Brd3 couple histone acetylation to transcription," Mol. Cell, 2008, 30(1):51-60.

Mochizuki et al., "The bromodomain protein Brd4 stimulates G1 gene transcription and promotes progression to S phase," J Biol. Chem. 2008, 283(14):9040-9048.

Peturssion et al., "Protecting Groups in Carbohydrate Chemistry," J Chem. Educ., 1997, 74(11):1297-1303.

Ravin, "Preformulation," Remington's Pharmaceutical Sciences, 17th Ed., (Mack Publishing Company, Easton, 1985), pp. 1409-1423.

Wang et al., "Brd2 disruption in mice causes severe obesity without Type 2 diabetes," Biochem. J., 2010, 425(1):71-83.

You et al., "Interaction of the bovine papillomavirus E2 protein with Brd4 tethers the viral DNA to host mitotic chromosomes," Cell, 2004, 117(3):349-60.

Zhu et al., "Reactivation of latent HIV-1 by inhibition of BRD4," Cell Reports, 2012, 2(4):807-816.

Zuber et al., "RNAi screen identifies Brd4 as a therapeutic target in acute myeloid leukaemia," Nature, 2011, 478(7370):524-528.

International Search Report and Written Opinion in International Application No. PCT/US2014/045543, mailed Sep. 10, 2014, 11 pages.

International Search Report and Written Opinion in International Application No. PCT/US2014/071102, mailed Feb. 13, 2015, 9 pages.

International Preliminary Report on Patentability in International Application No. PCT/US2014/027872, dated Sep. 24, 2015, 8 pages.

International Search Report and Written Opinion in International Application No. PCT/US2015/027047, dated Jul. 10, 2015, 14 pages.

TRICYCLIC HETEROCYCLES AS BET PROTEIN INHIBITORS

TECHNICAL FIELD

The present invention relates to tricyclic heterocycles which are inhibitors of BET proteins such as BRD2, BRD3, BRD4, and BRD-t and are useful in the treatment of diseases such as cancer.

BACKGROUND

The genomes of eukaryotic organisms are highly organized within the nucleus of the cell. DNA is packaged into chromatin by wrapping around a core of histone proteins to form a nucleosome. These nucleosomes are further compacted by aggregation and folding to form a highly condensed chromatin structure. A range of different states of condensation are possible, and the tightness of this structure varies during the cell cycle, being most compact during the process of cell division. Chromatin structure plays a critical role in regulating gene transcription by regulating protein access to the DNA. The chromatin structure is controlled by a series of post translational modifications to histone proteins, mainly within the tails of histones H3 and H4 that extend beyond the core nucleosome structure. These reversible modifications include acetylation, methylation, phosphorylation, ubiquitination and SUMOylation. These epigenetic marks are written and erased by specific enzymes that modify specific residues within the histone tail, thereby forming an epigenetic code. Other nuclear proteins bind to these marks and effect outputs specified by this information through the regulation of chromatin structure and gene transcription. Increasing evidence links genetic changes to genes encoding epigenetic modifiers and regulators leading to aberrant histone marks in diseases such as neurodegenerative disorders, metabolic diseases, inflammation and cancer.

Histone acetylation is typically associated with the activation of gene transcription, as the modification weakens the interaction between the DNA and the histone proteins, permitting greater access to DNA by the transcriptional machinery. Specific proteins bind to acetylated lysine residues within histones to "read" the epigenetic code. A highly conserved protein module called the bromodomain binds to acetylated lysine residues on histone and other proteins. There are more than 60 bromodomain-containing proteins in the human genome.

The BET (Bromodomain and Extra-Terminal) family of bromodomain containing proteins comprises 4 proteins (BRD2, BRD3, BRD4 and BRD-t) that share a conserved structural organization containing tandem N-terminal bromodomains capable of binding to acetylated lysine residues of histones and other proteins. BRD2, BRD3 and BRD4 are ubiquitously expressed while BRDt is restricted to germ cells. BRD proteins play essential, but non-overlapping roles in regulating gene transcription and controlling cell growth. BET proteins are associated with large protein complexes including Mediator, PAFc and super elongation complex that regulate many aspects of gene transcription. BRD2 and BRD4 proteins have been shown to remain in complex with chromosomes during mitosis and are required to promote transcription of critical genes including cyclin D and c-Myc that initiate the cell cycle (Mochizuki J Biol. Chem. 2008 283:9040-9048). BRD4 is essential for recruiting the protein translational elongation factor B complex to the promoters of inducible genes resulting in the phosphorylation of RNA polymerase II and stimulating productive gene transcription and elongation (Jang et al. Mol. Cell 2005 19:523-534). In some instances, a kinase activity of BRD4 may directly phosphorylate and activate RNA polymerase II (Devaiah et al. PNAS 2012 109:6927-6932). Cells lacking BRD4 show impaired progression through cell cycle. BRD2 and BRD3 are reported to associate with histones along actively transcribed genes and may be involved in facilitating transcriptional elongation (Leroy et al, Mol. Cell. 2008 30:51-60). In addition to acetylated histones, BET proteins have been shown to bind selectively to acetylated transcription factors including the RelA subunit of NF-kB and GATA1 thereby directly regulating the transcriptional activity of these proteins to control expression of genes involved in inflammation and hematopoietic differentiation (Huang et al, Mol. Cell. Biol. 2009 29:1375-1387; Lamonica Proc. Nat. Acad. Sci. 2011 108:E159-168).

A recurrent translocation involving NUT (nuclear protein in testes) with BRD3 or BRD4 to form a novel fusion oncogene, BRD-NUT, is found in a highly malignant form of epithelial neoplasia (French et al, Cancer Research 2003 63:304-307; French et al, Journal of Clinical Oncology 2004 22:4135-4139). Selective ablation of this oncogene restores normal cellular differentiation and reverses the tumorigenic phenotype (Filippakopoulos et al, Nature 2010 468:1068-1073). Genetic knockdown of BRD2, BRD3 and BRD4 has been shown to impair the growth and viability of a wide range of hematological and solid tumor cells (Zuber et al, Nature 2011 478:524-528; Delmore et al, Cell 2011 146:904-917). Aside from a role in cancer, BET proteins regulate inflammatory responses to bacterial challenge, and a BRD2 hypomorph mouse model showed dramatically lower levels of inflammatory cytokines and protection from obesity induced diabetes (Wang et al Biochem J. 2009 425:71-83; Belkina et al. J. Immunol 2013). In addition, some viruses make use of these BET proteins to tether their genomes to the host cell chromatin, as part of the process of viral replication or use BET proteins to facilitate viral gene transcription and repression (You et al, Cell 2004 117:349-60; Zhu et al, Cell Reports 2012 2:807-816).

Accordingly, there is a need for compounds that modulate the activity of the BET family of proteins, including BRD2, BRD3, and BRD4, that can be used to treat BET protein-associated diseases such as cancer. The compounds of the invention help meet this need.

SUMMARY

The present invention provides, inter alia, a compound of Formula (I):

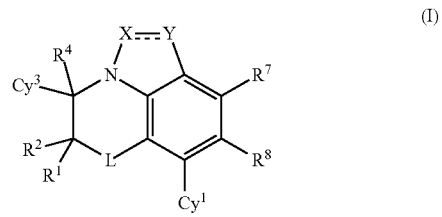

or a pharmaceutically acceptable salt thereof; wherein the variables are as defined below.

The present invention also provides a composition comprising a compound of Formula (I), or a pharmaceutically acceptable salt thereof, and at least one pharmaceutically acceptable carrier.

The present invention also provides methods of treating cancer and other diseases comprising administering to a patient a therapeutically effective amount of a compound of Formula (I), or a pharmaceutically acceptable salt thereof.

The present invention also provides use of a compound of the Formula (I), or a pharmaceutically acceptable salt thereof, for use in therapy.

The present invention also provides a compound of the Formula (I), or a pharmaceutically acceptable salt thereof, for use in the treatment of a disease referenced herein.

The details of one or more embodiments are set forth in the description below. Other features, objects, and advantages will be apparent from the description and from the claims.

DETAILED DESCRIPTION

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

I. Compounds

The present disclosure relates, inter alia, to a compound of a BET protein-inhibiting compound of Formula (I):

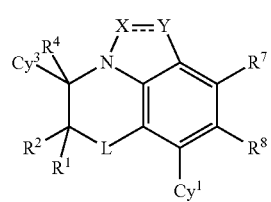

(I)

or a pharmaceutically acceptable salt thereof, wherein:

===== represents a single bond or a double bond;

L is $CR^9R^{9a}$, O, S, SO, or $SO_2$;

X is N or $NR^5$;

Y is N, $CR^6$, C(=O), or C(=S);

provided X is not $NR^5$ when Y is N;

$Cy^1$ is selected from phenyl and a 5-6 membered heteroaryl group comprising carbon and 1, 2, 3 or 4 heteroatoms selected from N, O and S, wherein said phenyl and 5-6 membered heteroaryl of $Cy^1$ are optionally substituted with 1, 2, 3, or 4 groups independently selected from $R^{11}$;

$R^1$ and $R^2$ are independently selected from H, halo, CN, OH, $C_{1-6}$ alkyl, $C_{2-6}$ alkenyl, $C_{2-6}$ alkynyl, $C_{1-6}$ haloalkyl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)NR^{c1}R^{d1}$, $NR^{c1}C(=O)OR^{a1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$, wherein said $C_{1-6}$ alkyl, $C_{2-6}$ alkenyl, and $C_{2-6}$ alkynyl of $R^1$ and $R^2$ are optionally substituted with 1, 2, or 3 groups independently selected from halo, CN, OH, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)NR^{c1}R^{d1}$, $NR^{c1}C(=O)OR^{a1}$, $S(=O)R^{b1}$, $S(=O)NR^{c1}R^{d1}$, $S(=O)_2R^{b1}$, $NR^{c1}S(=O)_2R^{b1}$ and $S(=O)_2NR^{c1}R^{d1}$;

provided $R^1$ and $R^2$ are other than Cl, Br, I, CN, and OH when L is O or S;

alternatively, $R^1$ and $R^2$ together with the carbon atom to which they are attached form a $C_{3-7}$ cycloalkyl group, wherein said cycloalkyl group is optionally substituted with 1, 2, 3, or 4 groups independently selected from $R^{20}$;

$Cy^3$ is selected from phenyl, $C_{3-7}$ cycloalkyl, a 5-10 membered heteroaryl group comprising carbon and 1, 2, 3 or 4 heteroatoms selected from N, O and S, and a 4-10 membered heterocycloalkyl group comprising carbon and 1, 2, or 3 heteroatoms selected from N, O and S, wherein said phenyl, $C_{3-7}$ cycloalkyl, 5-10 membered heteroaryl, and 4-10 membered heterocycloalkyl of $Cy^3$ are optionally substituted with 1, 2, 3, or 4 groups independently selected from $R^{13}$, wherein a ring-forming nitrogen atom of said 5-10 membered heteroaryl group or a ring-forming nitrogen atom of said 4-10 membered heterocycloalkyl group is optionally oxidized;

$R^4$ is H or $C_{1-6}$ alkyl;

$R^5$ is selected from H, $C_{1-6}$ alkyl, $C_{2-6}$ alkenyl, $C_{2-6}$ alkynyl, $C_{1-6}$ haloalkyl, phenyl, $C_{3-7}$ cycloalkyl, a 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{1-6}$ alkyl, phenyl, $C_{3-7}$ cycloalkyl, 5-6 membered heteroaryl, and 4-7 membered heterocycloalkyl of $R^5$ are optionally substituted by 1, 2, 3, or 4 groups independently selected from $R^{15}$;

$R^6$ is selected from H, halo, CN, OH, $OR^{a6}$, $SR^{a6}$, C(=O)$R^{b6}$, C(=O)$NR^{c6}R^{d6}$, C(=O)$OR^{a6}$, OC(=O)$R^{c6}$, OC(=O)$NR^{c6}R^{d6}$, $NR^{c6}R^{d6}$, $NR^{c6}C(=O)R^{b6}$, $NR^{c6}C(=O)NR^{c6}R^{d6}$, $NR^{c6}C(=O)OR^{a6}$, $S(=O)R^{b6}$, $S(=O)NR^{c6}R^{d6}$, $S(=O)_2R^{b6}$, $NR^{c6}S(=O)_2R^{b6}$, $S(=O)_2NR^{c6}R^{d6}$, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, $C_{2-6}$ alkynyl of $R^6$ are each optionally substituted by 1, 2, 3, or 4 groups independently selected from $R^{16}$;

alternatively, $R^6$ is selected from $C_{6-10}$ aryl, $C_{3-7}$ cycloalkyl, a 5-10 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{6-10}$ aryl, $C_{3-7}$ cycloalkyl, 5-10 membered heteroaryl, and 4-7 membered heterocycloalkyl of $R^6$ are each optionally substituted by 1, 2, 3, or 4 groups independently selected from $R^{20}$;

$R^7$ is selected from H, halo, CN, $OR^a$, $NR^cR^d$, $SR^b$, $CONR^cR^d$, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{1-6}$ alkyl, $C_{2-6}$ alkenyl, $C_{2-6}$ alkynyl, phenyl, $C_{3-7}$ cycloalkyl, 5-6 membered heteroaryl group, and 4-7 membered heterocycloalkyl group of $R^7$ are optionally substituted with 1, 2, or 3 groups independently selected from $R^{17}$;

$R^8$ is selected from H, $C_{1-3}$ alkyl, $C_{2-3}$ alkenyl, $C_{2-3}$ alkynyl, $C_{1-3}$ haloalkyl, halo, CN, $OR^a$, $NR^cR^d$, $SR^b$, and $CONR^cR^d$, wherein said $C_{1-3}$ alkyl, $C_{2-3}$ alkenyl, and $C_{2-3}$ alkynyl of $R^8$ are optionally substituted with 1, 2, or 3 groups independently selected from $R^{11}$;

$R^9$ and $R^{9a}$ are independently selected from H, $C_{1-3}$ alkyl, $C_{1-3}$ haloalkyl, halo, CN, $OR^a$, $NR^cR^d$, $SR^b$, and $CONR^cR^d$;

$R^{11}$ is independently at each occurrence selected from H, $C_{1-3}$ alkyl, $C_{1-3}$ haloalkyl, halo, CN, $OR^a$, $NR^cR^d$, $SR^b$, and $CONR^cR^d$;

$R^{13}$ is independently at each occurrence selected from H, halo, CN, OH, $C_{1-6}$ alkyl, $C_{2-6}$ alkenyl, $C_{2-6}$ alkynyl, $C_{1-6}$ haloalkyl, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $S(=O)R^{b3}$, $S(=O)NR^{c3}R^{d3}$, $S(=O)_2R^{b3}$, $NR^{c3}S(=O)_2R^{b3}$ and $S(=O)_2NR^{c3}R^{d3}$, wherein said $C_{1-6}$ alkyl, $C_{2-6}$ alkenyl, and $C_{2-6}$ alkynyl of $R^{13}$ are optionally substituted with 1, 2, or 3 groups independently selected from halo, CN, OH, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $S(=O)R^{b3}$, $S(=O)NR^{c3}R^{d3}$, $S(=O)_2R^{b3}$, $NR^{c3}S(=O)_2R^{b3}$ and $S(=O)_2NR^{c3}R^{d3}$;

$R^{15}$ is independently at each occurrence selected from H, halo, CN, OH, $C_{1-6}$ alkyl, $C_{2-6}$ alkenyl, $C_{2-6}$ alkynyl, $C_{1-6}$ haloalkyl, $OR^{a5}$, $SR^{a5}$, $C(=O)R^{b5}$, $C(=O)NR^{c5}R^{c5}$, $C(=O)OR^{a5}$, $OC(=O)R^{b5}$, $OC(=O)NR^{c5}R^{c5}$, $NR^{c5}R^{c5}$, $NR^{c5}C(=O)R^{b5}$, $NR^{c5}C(=O)NR^{c5}R^{c5}$, $NR^{c5}C(=O)OR^{a5}$, $S(=O)R^{b5}$, $S(=O)NR^{c5}R^{c5}$, $S(=O)_2R^{b5}$, $NR^{c5}S(=O)_2R^{b5}$ and $S(=O)_2NR^{c5}R^{d5}$, wherein said $C_{1-6}$ alkyl, $C_{2-6}$ alkenyl, and $C_{2-6}$ alkynyl of $R^{15}$ are optionally substituted with 1, 2, or 3 groups independently selected from halo, CN, OH, $OR^{a5}$, $SR^{a5}$, $C(=O)R^{b5}$, $C(=O)NR^{c5}R^{c5}$, $C(=O)OR^{a5}$, $OC(=O)R^{b5}$, $OC(=O)NR^{c5}R^{c5}$, $NR^{c5}R^{c5}$, $NR^{c5}C(=O)R^{b5}$, $NR^{c5}C(=O)NR^{c5}R^{c5}$, $NR^{c5}C(=O)OR^{a5}$, $S(=O)R^{b5}$, $S(=O)NR^{c5}R^{c5}$, $S(=O)_2R^{b5}$, $NR^{c5}S(=O)_2R^{b5}$ and $S(=O)_2NR^{c5}R^{d5}$;

$R^{16}$ is independently at each occurrence selected from halo, CN, OH, $OR^{a6}$, $SR^{a6}$, $C(=O)R^{b6}$, $C(=O)NR^{c6}R^{d6}$, $C(=O)OR^{a6}$, $OC(=O)R^{b6}$, $OC(=O)NR^{c6}R^{d6}$, $NR^{c6}R^{d6}$, $NR^{c6}C(=O)R^{b6}$, $NR^{c6}C(=O)NR^{c6}R^{d6}$, $NR^{c6}C(=O)OR^{a6}$, $S(=O)R^{b6}$, $S(=O)NR^{c6}R^{d6}$, $S(=O)_2R^{b6}$, $NR^{c6}S(=O)_2R^{b6}$, $S(=O)_2NR^{c6}R^{d6}$, $C_{6-10}$ aryl, $C_{3-7}$ cycloalkyl, a 5-10 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{6-10}$ aryl, $C_{3-7}$ cycloalkyl, 5-10 membered heteroaryl, and 4-7 membered heterocycloalkyl of $R^{16}$ are each optionally substituted by 1, 2, 3, or 4 groups independently selected $R^{20}$;

$R^{17}$ and $R^{18}$ are independently at each occurrence selected from halo, CN, $OR^a$, $NR^cR^d$, $SR^b$, and $CONR^cR^d$;

$R^a$, $R^c$, and $R^d$ are independently at each occurrence selected from H and $C_{1-6}$ alkyl;

$R^b$ is at each occurrence $C_{1-6}$ alkyl;

$R^{a1}$, $R^{b1}$, $R^{c1}$ and $R^{d1}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a1}$, $R^{b1}$, $R^{c1}$ and $R^{d1}$ are each optionally substituted with 1, 2, or 3 substituents independently selected from $R^{20}$;

$R^{a3}$, $R^{b3}$, $R^{c1}$ and $R^{d3}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a3}$, $R^{b3}$, $R^{c1}$ and $R^{d3}$ are each optionally substituted with 1, 2, or 3 substituents independently selected from halo, CN, OH, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$, $NR^{c4}C(=O)R^{b4}$, $NR^{c4}C(=O)NR^{c4}R^{d4}$, $NR^{c4}C(=O)OR^{a4}$, $S(=O)R^{b4}$, $S(=O)NR^{c4}R^{d4}$, $S(=O)_2R^{b4}$, $NR^{c4}S(=O)_2R^{b4}$ and $S(=O)_2NR^{c4}R^{d4}$;

$R^{a4}$, $R^{b4}$, $R^{c4}$ and $R^{d4}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a4}$, $R^{b4}$, $R^{c4}$ and $R^{d4}$ are each optionally substituted with 1, 2, or 3 substituents independently selected from $R^{20}$;

$R^{a5}$, $R^{b5}$, $R^{c5}$ and $R^{d5}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a5}$, $R^{b5}$, $R^{c5}$ and $R^{d5}$ are each optionally substituted with 1, 2, or 3 substituents independently selected from $R^{20}$;

$R^{a6}$, $R^{c6}$ and $R^{d6}$ are independently at each occurrence selected from H, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl group, and 4-7 membered heterocycloalkyl group forming $R^{a6}$, $R^{c6}$ and $R^{d6}$ are each optionally substituted with 1, 2, or 3 substituents independently selected from $R^{20}$;

alternatively, $R^{c6}$ and $R^{d6}$ together with the nitrogen atom to which they are attached may be combined to form a 4-7 membered heterocycloalkyl group comprising carbon, nitrogen, and 0, 1, or 2 additional heteroatoms selected from N, O and S, wherein said 4-7 membered heterocycloalkyl group is optionally substituted with 1, 2, or 3 substituents independently selected from $R^{20}$;

$R^{b6}$ is independently at each occurrence selected from $C_{1-6}$ alkyl, $C_{2-6}$ alkenyl, $C_{2-6}$ alkynyl, $C_{1-6}$ haloalkyl, phenyl, $C_{3-7}$ cycloalkyl, a 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl group, and 4-7 membered heterocycloalkyl group are each optionally substituted with 1, 2, or 3 substituents independently selected from $R^{20}$; and $R^{20}$ is at each occurrence independently selected from H, halo, OH, CN, amino, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, $C_{1-4}$ haloalkoxy, $C_{1-4}$ alkyl-$C(=O)$—, $C_{1-4}$ alkyl-$C(=O)O$—, $C_{1-4}$ alkyl-$OC(=O)$—, $HOC(=O)$—, $H_2NC(=O)$—, $C_{1-4}$ alkyl-$NHC(=O)$—, di($C_{1-4}$ alkyl)$NC(=O)$—, $C_{1-4}$ alkyl-$C(=O)NH$—, $C_{1-4}$ alkyl-$S(=O)$—, $H_2NS(=O)$—, $C_{1-4}$ alkyl-$NHS(=O)$—, di($C_{1-4}$ alkyl)$NS(=O)$—, $C_{1-4}$ alkyl-$S(=O)_2$—, $C_{1-4}$ alkyl-$S(=O)_2NH$—, $H_2NS(=O)_2$—, $C_{1-4}$ alkyl-$NHS(=O)_2$—, and di($C_{1-4}$ alkyl)$NS(=O)_2$—.

In some embodiments, L is O.

In some embodiments, L is S.

In some embodiments, L is $CR^9CR^{9a}$.

In some embodiments, L is $CH_2$.

In some embodiments, X is N.

In some embodiments, X is NR⁵.

In some embodiments, Y is CR⁶.

In some embodiments, Y is C(=O).

In some embodiments, X=Y is N=N.

In some embodiments, Cy¹ is isoxazolyl substituted with 1 or 2 groups independently selected from R¹¹.

In some embodiments, Cy¹ is pyrazolyl substituted with 1 or 2 groups independently selected from R¹¹.

In some embodiments, R¹ is selected from H, methyl, —C(=O)OCH₂CH₃, —C(=O)N(H)CH₂CH₃, —C(=O)N(H)CH₂CH₂OH, and —C(=O)N(CH₃)₂.

In some embodiments, R¹ is H.

In some embodiments, R¹ is methyl.

In some embodiments, R² is H.

In some embodiments, Cy³ is selected from phenyl, pyridinyl, oxidopyridinyl, thiazolyl, cyclohexyl, dihydrobenzofuranyl and tetrahydrofuranyl, wherein said phenyl, pyridinyl, oxidopyridinyl, thiazolyl, cyclohexyl, dihydrobenzofuranyl and tetrahydrofuranyl is optionally substituted with 1, 2, 3, or 4 groups independently selected from R¹³.

In some embodiments, Cy³ is phenyl optionally substituted with 1, 2, 3, or 4 groups independently selected from R¹³.

In some embodiments, Cy³ is pyridinyl optionally substituted with 1, 2, 3, or 4 groups independently selected from R¹³.

In some embodiments, Cy³ is oxidopyridinyl optionally substituted with 1, 2, 3, or 4 groups independently selected from R¹³.

In some embodiments, Cy³ is thiazolyl optionally substituted with 1, 2, 3, or 4 groups independently selected from R¹³.

In some embodiments, Cy³ is cyclohexyl optionally substituted with 1, 2, 3, or 4 groups independently selected from R¹³.

In some embodiments, Cy³ is dihydrobenzofuranyl optionally substituted with 1, 2, 3, or 4 groups independently selected from R¹³.

In some embodiments, Cy³ is tetrahydrofuranyl optionally substituted with 1, 2, 3, or 4 groups independently selected from R¹³.

In some embodiments, R⁵ is methyl.

In some embodiments, R⁵ is H.

In some embodiments, R⁶ is H, $C_{1-6}$ alkoxy, $C_{1-6}$ alkyl, $C_{2-6}$ alkenyl, $C_{2-6}$ alkynyl, or $C_{1-6}$ haloalkyl.

In some embodiments, R⁶ is H.

In some embodiments, R⁶ is methoxy.

In some embodiments, R⁷ is selected from H, halo, $C_{1-4}$ alkyl, and CN.

In some embodiments, R⁷ is selected from H, Br, F, methyl, and CN.

In some embodiments, R⁷ is H.

In some embodiments, R⁷ is Br.

In some embodiments, R⁷ is F.

In some embodiments, R⁷ is methyl.

In some embodiments, R⁷ is CN.

In some embodiments, R⁸ is selected from H, halo, $C_{1-4}$ alkyl, and CN.

In some embodiments, R⁸ is H.

In some embodiments, the compounds of the invention have Formula (IIa), (IIb), or (IIc):

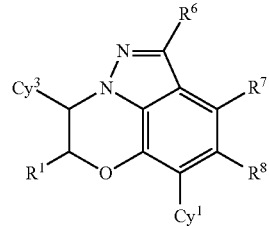

(IIa)

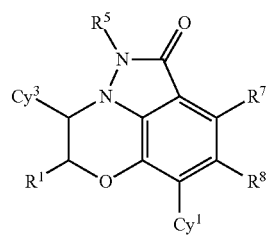

(IIb)

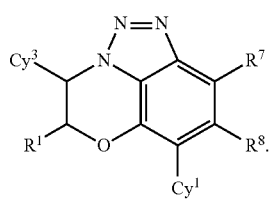

(IIc)

In some embodiments, the compounds of the invention have Formula (IIIa), (IIIb), or (IIIc):

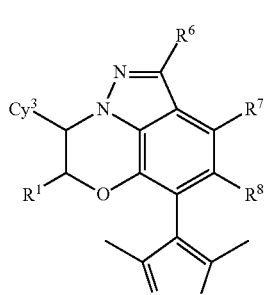

(IIIa)

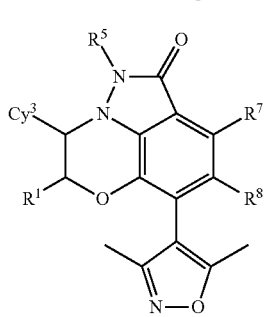

(IIIb)

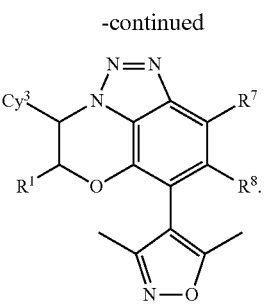

(IIIc)

In some embodiments:

L is O or S;

Y is N, CR$^6$, or C(=O);

Cy$^1$ is a 5-6 membered heteroaryl group comprising carbon and 1, 2, 3 or 4 heteroatoms selected from N, O and S, wherein said 5-6 membered heteroaryl of Cy$^1$ is optionally substituted with 1, 2, 3, or 4 groups independently selected from R$^{11}$;

R$^1$ is selected from H, F, C$_{1-6}$ alkyl, C$_{2-6}$ alkenyl, C$_{2-6}$ alkynyl, C$_{1-6}$ haloalkyl, OR$^{a1}$, C(=O)R$^{b1}$, C(=O)NR$^{c1}$R$^{d1}$, C(=O)OR$^{a1}$, NR$^{c1}$R$^{d1}$, and NR$^{c1}$C(=O)R$^{b1}$, wherein said C$_{1-6}$ alkyl, C$_{2-6}$ alkenyl, and C$_{2-6}$ alkynyl of R$^1$ is optionally substituted with 1, 2, or 3 groups independently selected from halo, CN, OH, OR$^{a1}$, C(=O)R$^{b1}$, C(=O)NR$^{c1}$R$^{d1}$, C(=O)OR$^{a1}$, NR$^{c1}$R$^{d1}$, and NR$^{c1}$C(=O)R$^{b1}$; provided R$^1$ is not OH;

R$^7$ is selected from H, halo, CN, OR$^a$, C$_{1-6}$ alkyl, C$_{1-6}$ haloalkyl, phenyl, C$_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said C$_{1-6}$ alkyl, phenyl, C$_{3-7}$ cycloalkyl, 5-6 membered heteroaryl group, and 4-7 membered heterocycloalkyl group of R$^7$ are optionally substituted with 1, 2, or 3 groups independently selected from R$^{17}$;

R$^8$ is selected from H and C$_{1-3}$ alkyl; and

R$^{a1}$, R$^{b1}$, R$^{c1}$ and R$^{d1}$ are independently at each occurrence selected from H, C$_{1-6}$ alkyl, and C$_{1-6}$ haloalkyl.

In some embodiments:

L is O;

Y is N, CR$^6$, or C(=O);

Cy$^1$ is a 5-membered heteroaryl group comprising carbon and 1, 2, 3 or 4 heteroatoms selected from N, O and S, wherein said 5-membered heteroaryl of Cy$^1$ is optionally substituted with 1, 2, 3, or 4 groups independently selected from R$^{11}$;

R$^1$ and R$^2$ are both H;

Cy$^3$ is selected from phenyl and a 5-6 membered heteroaryl group comprising carbon and 1, 2, 3 or 4 heteroatoms selected from N, O and S, wherein said phenyl and 5-6 membered heteroaryl of Cy$^3$ are optionally substituted with 1, 2, 3, or 4 groups independently selected from R$^{13}$, wherein a ring-forming nitrogen atom of said 5-6 membered heteroaryl group;

R$^4$ is H;

R$^5$ is selected from H and C$_{1-6}$ alkyl;

R$^6$ is selected from H, OR$^{a6}$;

R$^7$ is selected from H and halo; and

R$^8$ is H.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the phrase "optionally substituted" means unsubstituted or substituted. As used herein, the term "substituted" means that a hydrogen atom is removed and replaced by a substituent. It is to be understood that substitution at a given atom is limited by valency. Throughout the definitions, the term "C$_{n-m}$" indicates a range which includes the endpoints, wherein n and m are integers and indicate the number of carbons. Examples include C$_{1-4}$, C$_{1-6}$, and the like.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the term "C$_{n-m}$ alkyl", employed alone or in combination with other terms, refers to a saturated hydrocarbon group that may be straight-chain or branched, having n to m carbons. In some embodiments, the alkyl group contains from 1 to 6 carbon atoms or from 1 to 4 carbon atoms, or from 1 to 3 carbon atoms. Examples of alkyl moieties include, but are not limited to, chemical groups such as methyl, ethyl, n-propyl, isopropyl, n-butyl, s-butyl, and t-butyl.

As used herein, the term "C$_{n-m}$ alkoxy", employed alone or in combination with other terms, refers to a group of formula —O-alkyl, wherein the alkyl group has n to m carbons. Example alkoxy groups include methoxy, ethoxy, and propoxy (e.g., n-propoxy and isopropoxy). In some embodiments, the alkyl group has 1 to 3 carbon atoms.

As used herein, "C$_{n-m}$ alkenyl" refers to an alkyl group having one or more double carbon-carbon bonds and having n to m carbons. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "C$_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "C$_{n-m}$ alkylamino" refers to a group of formula —NH(alkyl), wherein the alkyl group has n to m carbon atoms. In some embodiments, the alkyl group has 1 to 6 or 1 to 4 carbon atoms.

As used herein, the term "di-C$_{n-m}$-alkylamino" refers to a group of formula —N(alkyl)$_2$, wherein the two alkyl groups each has, independently, n to m carbon atoms. In some embodiments, each alkyl group independently has 1 to 6 or 1 to 4 carbon atoms.

As used herein, the term "C$_{n-m}$ alkylthio" refers to a group of formula —S-alkyl, wherein the alkyl group has n to m carbon atoms. In some embodiments, the alkyl group has 1 to 6 or 1 to 4 carbon atoms.

As used herein, the term "amino" refers to a group of formula —NH$_2$.

As used herein, the term "aryl," employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is C$_{6-10}$ aryl. In some embodiments, the aryl group is a naphthalene ring or phenyl ring. In some embodiments, the aryl group is phenyl.

As used herein, the term "carbonyl", employed alone or in combination with other terms, refers to a —C(O)— group.

As used herein, the term "cycloalkyl", employed alone or in combination with other terms, refers to a non-aromatic cyclic hydrocarbon moiety, which may optionally contain one or more alkenylene groups as part of the ring structure. Cycloalkyl groups can include mono- or polycyclic (e.g., having 2, 3 or 4 fused rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is $C_{3-7}$ cycloalkyl, which is monocyclic or bicyclic. Examplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, the cycloalkyl group is cyclopropyl, cyclobutyl, cyclopentyl, or cyclohexyl.

As used herein, "$C_{n-m}$ haloalkoxy" refers to a group of formula —O-haloalkyl having n to m carbon atoms. An example haloalkoxy group is $OCF_3$. An additional example haloalkoxy group is $OCHF_2$. In some embodiments, the haloalkoxy group is fluorinated only. In some embodiments, the alkyl group has 1 to 6 or 1 to 4 carbon atoms.

As used herein, the term "halo" refers to a halogen atom selected from F, Cl, I or Br. In some embodiments, "halo" refers to a halogen atom selected from F, Cl, or Br. In some embodiments, exemplary halo groups are F.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the alkyl group has 1 to 6 or 1 to 4 carbon atoms.

As used herein, the term "heteroaryl", employed alone or in combination with other terms, refers to a monocyclic or polycyclic (e.g., having 2, 3 or 4 fused rings) aromatic hydrocarbon moiety, having one or more heteroatom ring members selected from nitrogen, sulfur and oxygen. In some embodiments, heteroaryl is 5- to 10-membered $C_{1-9}$ heteroaryl, which is monocyclic or bicyclic and which has 1, 2, 3, or 4 heteroatom ring members independently selected from nitrogen, sulfur and oxygen. When the heteroaryl group contains more than one heteroatom ring member, the heteroatoms may be the same or different. The nitrogen atoms in the ring(s) of the heteroaryl group can be oxidized to form N-oxides. Example heteroaryl groups include, but are not limited to, pyridine, pyrimidine, pyrazine, pyridazine, pyrrole, pyrazole, azolyl, oxazole, isoxazole, thiazole, isothiazole, imidazole, furan, thiophene, triazole, tetrazole, thiadiazole, quinoline, isoquinoline, indole, benzothiophene, benzofuran, benzisoxazole, imidazo[1,2-b]thiazole, purine, triazine or the like.

A 5-membered heteroaryl is a heteroaryl group having five ring atoms comprising carbon and one or more (e.g., 1, 2, or 3) ring atoms independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A 6-membered heteroaryl is a heteroaryl group having six ring atoms wherein one or more (e.g., 1, 2, or 3) ring atoms are nitrogen. Exemplary six-membered ring heteroaryls are pyridyl, pyrazinyl, pyrimidinyl, triazinyl and pyridazinyl.

As used herein, the term "heterocycloalkyl", employed alone or in combination with other terms, refers to non-aromatic ring system, which may optionally contain one or more alkenylene or alkynylene groups as part of the ring structure, and which has at least one heteroatom ring member independently selected from nitrogen, sulfur and oxygen. When the heterocycloalkyl group contains more than one heteroatom, the heteroatoms may be the same or different. Heterocycloalkyl groups can include mono- or polycyclic (e.g., having 2, 3 or 4 fused rings) ring systems, including spiro systems. Also included in the definition of heterocycloalkyl are moieties that have one or more aromatic rings fused (i.e., having a bond in common with) to the non-aromatic ring, for example, 1,2,3,4-tetrahydro-quinoline, dihydrobenzofuran and the like. The carbon atoms or heteroatoms in the ring(s) of the heterocycloalkyl group can be oxidized to form a carbonyl, or sulfonyl group (or other oxidized linkage) or a nitrogen atom can be quaternized. In some embodiments, heterocycloalkyl is 5- to 10-membered $C_{2-9}$ heterocycloalkyl, which is monocyclic or bicyclic and which has 1, 2, 3, or 4 heteroatom ring members independently selected from nitrogen, sulfur and oxygen. Examples of heterocycloalkyl groups include 1,2,3,4-tetrahydro-quinoline, dihydrobenzofuran, azetidine, azepane, pyrrolidine, piperidine, piperazine, morpholine, thiomorpholine, and pyran.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

When the compounds of the invention contain a chiral center, the compounds can be any of the possible stereoisomers. In compounds with a single chiral center, the stereochemistry of the chiral center can be (R) or (S). In compounds with two chiral centers, the stereochemistry of the chiral centers can each be independently (R) or (S) so the configuration of the chiral centers can be (R) and (R), (R) and (S); (S) and (R), or (S) and (S). In compounds with three chiral centers, the stereochemistry each of the three chiral centers can each be independently (R) or (S) so the configuration of the chiral centers can be (R), (R) and (R); (R), (R) and (S); (R), (S) and (R); (R), (S) and (S); (S), (R) and (R); (S), (R) and (S); (S), (S) and (R); or (S), (S) and (S).

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone enol pairs, amide-imidic acid pairs, lactam lactim pairs, amide-imidic acid pairs, enamine imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers.

The term, "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified (e.g., in the case of purine rings, unless otherwise indicated, when the compound name or structure has the 9H tautomer, it is understood that the 7H tautomer is also encompassed).

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in a compound of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19, and in Stahl et al., *Handbook of Pharmaceutical Salts: Properties, Selection, and Use*, (Wiley, 2002). In some embodiments, the compounds described herein include the N-oxide forms.

The following abbreviations may be used herein: AcOH (acetic acid); Ac$_2$O (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DIAD (N,N'-diisopropyl azidodicarboxylate); DIPEA (N,N-diisopropylethylamine); DMF (N,N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography mass spectrometry); m (multiplet); M (molar); mCPBA (3-chloroperoxybenzoic acid); MgSO$_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaHCO$_3$ (sodium bicarbonate); NaOH (sodium hydroxide); Na$_2$SO$_4$ (sodium sulfate); NH$_4$Cl (ammonium chloride); NH$_4$OH (ammonium hydroxide); nM (nanomolar); NMR (nuclear magnetic resonance spectroscopy); OTf (trifluoromethanesulfonate); Pd (palladium); Ph (phenyl); pM (picomolar); POCl$_3$ (phosphoryl chloride); RP-HPLC (reverse phase high performance liquid chromatography); s (singlet); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); μg (microgram(s)); μL (microliter(s)); μM (micromolar); wt % (weight percent).

II. Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, 4$^{th}$ Ed., Wiley & Sons, Inc., New York (2006), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) (*"Preparative LC-MS Purification: Improved Compound Specific Method Optimization"* Karl F. Blom, Brian Glass, Richard Sparks, Andrew P. Combs *J. Combi. Chem.* 2004, 6(6), 874-883, which is incorporated herein by reference in its entirety) and normal phase silica chromatography.

Compounds of Formula (I) can be formed as shown in Scheme I. The phenols (L=O) or thiols (L=S) (i) can be nitrated using standard conditions (HNO$_3$/H$_2$SO$_4$) and esterified using standard conditions (SOCl$_2$/MeOH or (COCl)$_2$/MeOH) to give (iii). Phenol (iii) can be protected (e.g., protecting group P=benzyl) to give (iv). The halo group of (iv) can be coupled to M-Cy$^1$, where M is a boronic acid, boronic ester or an appropriately substituted metal (e.g., Cy$^1$-M is Cy$^1$-B(OH)$_2$, Cy$^1$-Sn(Bu)$_4$, or Zn—Cy$^1$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give compounds (v). Alternatively, M-Cy$^1$ can be an amine containing heterocycle (where M is H and is attached to the amine nitrogen of the heterocycle Cy$^1$) with coupling to compound (iv) being performed by heating with a base or under Buchwald conditions (e.g., in the presence of a palladium(0) catalyst, such as tetrakis(triphenylphosphine)palladium(0) and a base (e.g., an alkoxide base)) to give compounds (v). The nitro group of (v) can be reduced under standard conditions (e.g., Pd, Fe or Zn) to give the amino compound which can be deprotected if necessary to give (vi). Aniline (vi) can be alkylated using standard alkylating conditions with Cy$^3$COC(R$^1$R$^2$)—X (ii) (X=leaving group, such as halo (Br, Cl, or I) or mesylate) or Mitsunobu conditions (e.g., Cy$^3$COC(R$^1$R$^2$)—X (ii) (X=OH), DEAD, Ph$_3$P) to afford ether or thioether derivatives (vii). The imine of compound (vii) can be reduced (e.g., hydrogenation with palladium) to give compound (viii) (R$^4$=H) or treated with a Grignard reagent of formula R$^4$—MgX$^1$ (X$^1$=halo) to give (viii). Treatment of compound (viii) with sodium nitrite can give compound (ix). Reduction of nitroso (ix) (e.g., sodium dithionite, zinc with acetic acid, or zinc with saturated aqueous ammonium chloride) gives the hydrazine which can cyclize (in situ or with heat) with the adjacent ester to give compounds of Formula (I) (x). Compound (x) can be alkylated (e.g., alkyl halide and a base, such as triethylamine, NaH or Na$_2$CO$_3$; or under Mitsunobu conditions) to afford the N-substituted derivatives of Formula (I) (xi) or O-substituted derivatives of Formula (I) (xii) (R$^6$=OR$^{a6}$).

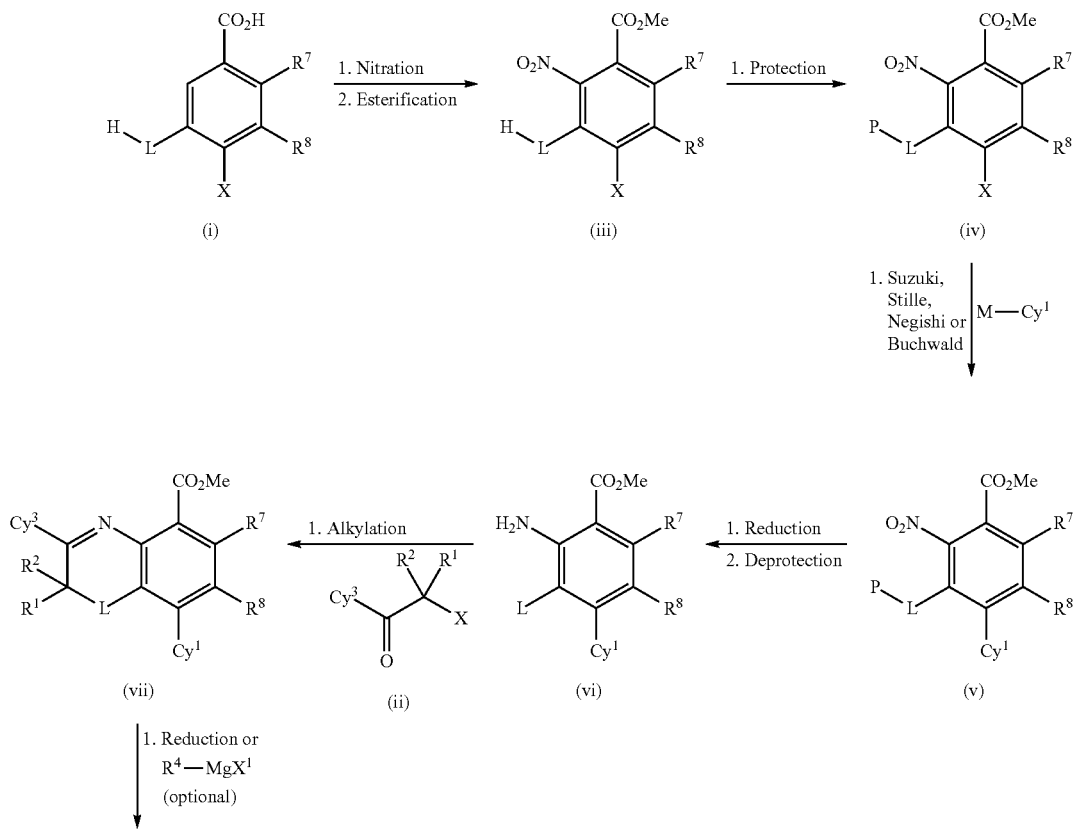

Scheme I

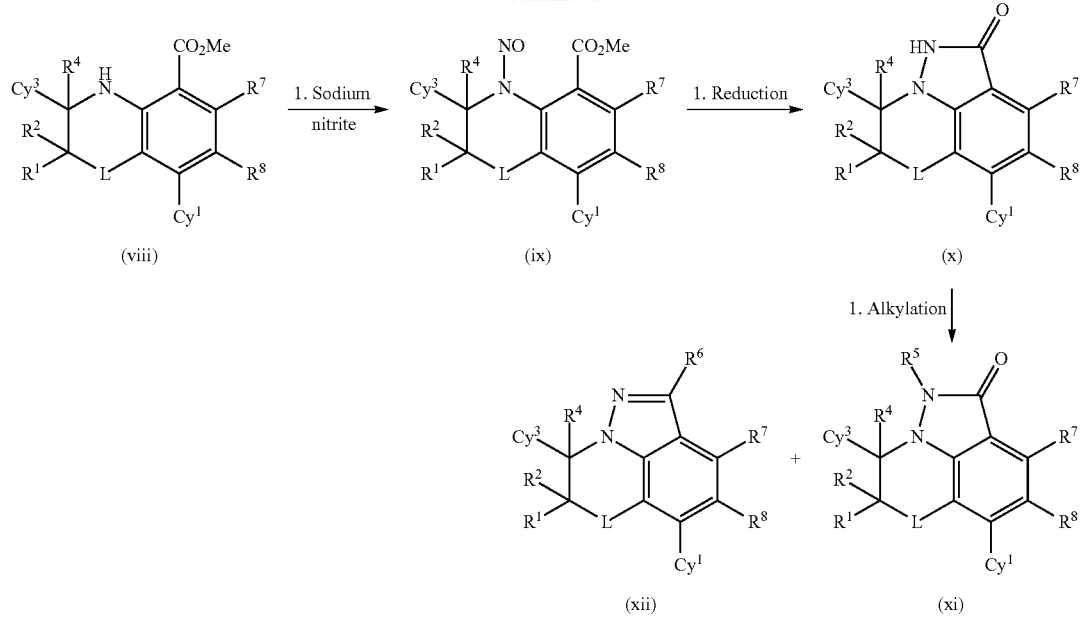

Compounds of Formula (I) can be formed as shown in Scheme II. Ester (i) (compound (viii) from Scheme 1) can be reduced under standard conditions (e.g., LAH) to give alcohol (ii). Treatment of (ii) with sodium nitrite followed by reduction (e.g., LAH) can give hydrazine (iii). Oxidation of alcohol (iii) to the aldehyde (e.g., Swern oxidation) and intramolecular cyclization with the hydrazine gives derivatives of Formula (I) (iv). Alternatively, compound (ii) can be oxidized (e.g., Swern oxidation) to give aldehyde (v). Aldehyde (v) may then be reacted with a Grignard reagent of formula $R^6$—$MgX^1$ ($X^1$=halo) to give alcohol (vi). Treatment of (vi) with sodium nitrite followed by reduction (e.g., LAH) can give hydrazine (vii). Oxidation of alcohol (vii) to the ketone (e.g., Swern oxidation) and intramolecular cyclization with the hydrazine gives derivatives of Formula (I) (viii).

Scheme II

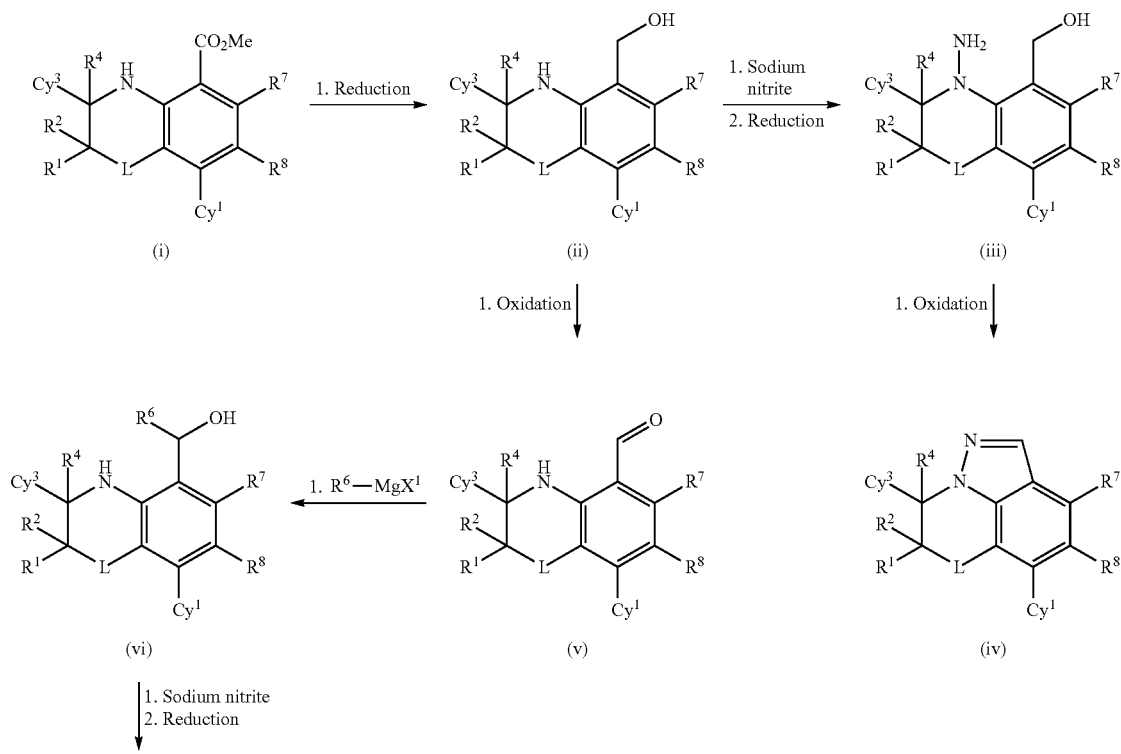

Compounds of Formula (I) can be formed as shown in Scheme III. Compounds (i) can be halogenated with N-chlorosuccinimide, N-bromosuccinimide or N-iodosuccinimide to give halide (ii) where X=Cl, Br or I. The halo group of (ii) can be coupled to M-R$^7$, where M is a boronic acid, boronic ester or an appropriately substituted metal (e.g., R$^7$-M is R$^7$—B(OH)$_2$, R$^7$—Sn(Bu)$_4$, or Zn—R$^7$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of Formula I (iii). Alternatively, M-R$^7$ can be an amine containing heterocycle (where M is H and is attached to the amine nitrogen of the heterocycle R$^7$) with coupling to compound (ii) being performed by heating with a base or under Buchwald conditions (e.g., in the presence of a palladium(0) catalyst, such as tetrakis(triphenylphosphine)palladium(0) and a base (e.g., an alkoxide base)) to give a derivative of Formula (I) (iii).

Compounds of Formula (I) can be formed as shown in Scheme IV. The phenols (L=O) or thiols (L=S) (i) can be alkylated using standard alkylating conditions with Cy$^3$COC(R$^1$R$^2$)—X (ii) (X=leaving group, such as halo (Br, Cl, or I) or mesylate) or Mitsunobu conditions (e.g., Cy$^3$COC(R$^1$R$^2$)—X (ii) (X=OH), DEAD, Ph$_3$P) to afford ether or thioether derivatives (iii). Cyclization in situ or upon heating can afford imine (iv) which upon treatment with a Grignard reagent of formula R$^4$—MgX$^1$ (X$^1$=halo) and reduction of the nitro group (e.g., H$_2$ Pd/C or Fe) can give an amine (v) or the Grignard treatment could be skipped to give amine (v) (R$^4$=H). Compounds (v) can be halogenated with N-chlorosuccinimide, N-bromosuccinimide or N-iodosuccinimide followed by treatment with sodium nitrite to give tricyclic halide (vi) where X=Cl, Br or I. The halo group of (vi) can be coupled to M-Cy$^1$, where M is a boronic acid, boronic ester or an appropriately substituted metal (e.g., Cy$^1$-M is Cy$^1$-B(OH)$_2$, Cy$^1$-Sn(Bu)$_4$, or Zn—Cy$^1$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of Formula (I) (vii). Alternatively, M-Cy$^1$ can be an amine containing heterocycle (where M is H and is attached to the amine nitrogen of the heterocycle Cy$^1$) with coupling to compound (vi) being performed by heating with a base or under Buchwald conditions (e.g., in the presence of a palladium(0) catalyst, such as tetrakis(triphenylphosphine)palladium(0) and a base (e.g., an alkoxide base)) to give a derivative of Formula (I) (vii).

Scheme IV

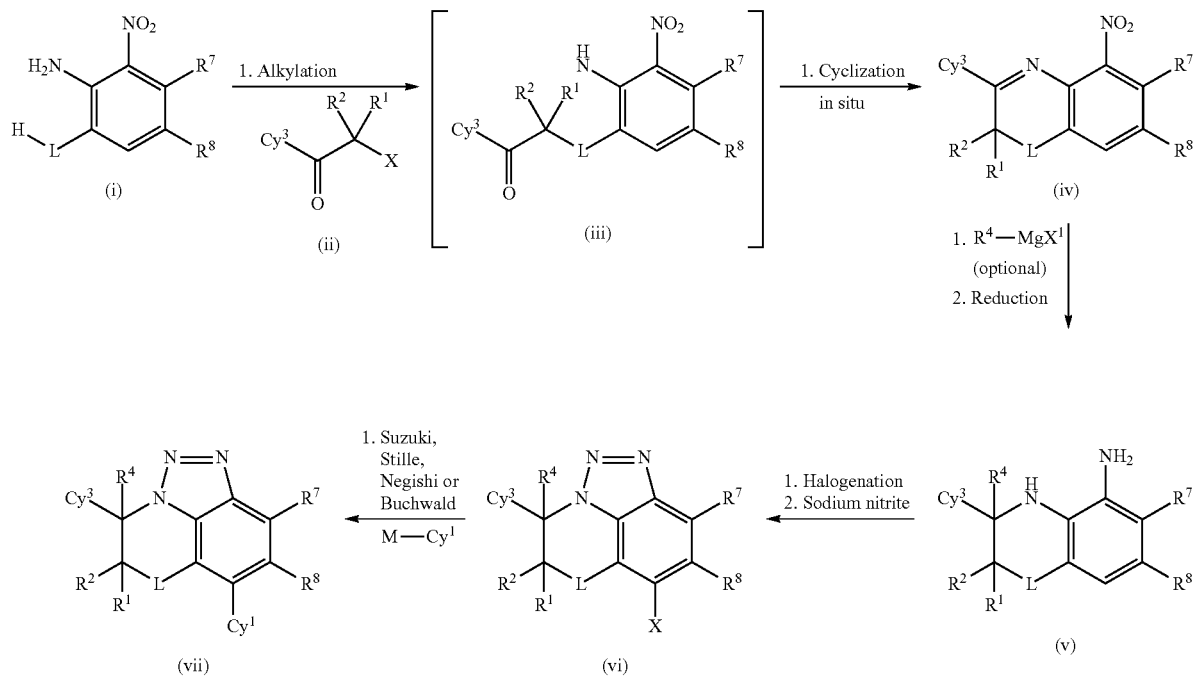

Compounds of Formula (I) can be formed as shown in Scheme V. The phenols (L=O) or thiols (L=S) (i) can be alkylated using standard alkylating conditions with Cy³COC(R¹R²)—X (ii) (X=leaving group, such as halo (Br, Cl, or I) or mesylate) or Mitsunobu conditions (e.g., Cy³COC(R¹R²)—X (ii) (X=OH), DEAD, Ph₃P) to afford ether or thioether derivatives (iii) after displacement of the fluorine with an appropriately protected amine (NH₂P where P is a protecting group). Reduction of the nitro group of (iii) under standard conditions (e.g., Fe or Zn) can give the amino compound which can cyclize in situ or upon heating to afford an imine which upon treatment with a Grignard reagent of formula R⁴—MgX¹ (X¹ halo) can give amine (iv) or the imine can just be reduced with hydrogen over Pd/C to give amine (iv) where R⁴=H. Compounds (iv) can be halogenated with N-chlorosuccinimide, N-bromosuccinimide or N-iodosuccinimide to give tricyclic halide (v) where X=Cl, Br or I followed by reaction to form the triazole with sodium nitrite. The halo group of (v) can be coupled to M-Cy¹, where M is a boronic acid, boronic ester or an appropriately substituted metal (e.g., Cy¹-M is Cy¹-B(OH)₂, Cy¹-Sn(Bu)₄, or Zn—Cy¹), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of Formula (I) (vi). Alternatively, M-Cy¹ can be an amine containing heterocycle (where M is H and is attached to the amine nitrogen of the heterocycle Cy¹) with coupling to compound (v) being performed by heating with a base or under Buchwald conditions (e.g., in the presence of a palladium(0) catalyst, such as tetrakis(triphenylphosphine) palladium(0) and a base (e.g., an alkoxide base)) to give a derivative of Formula (I) (vi).

Scheme V

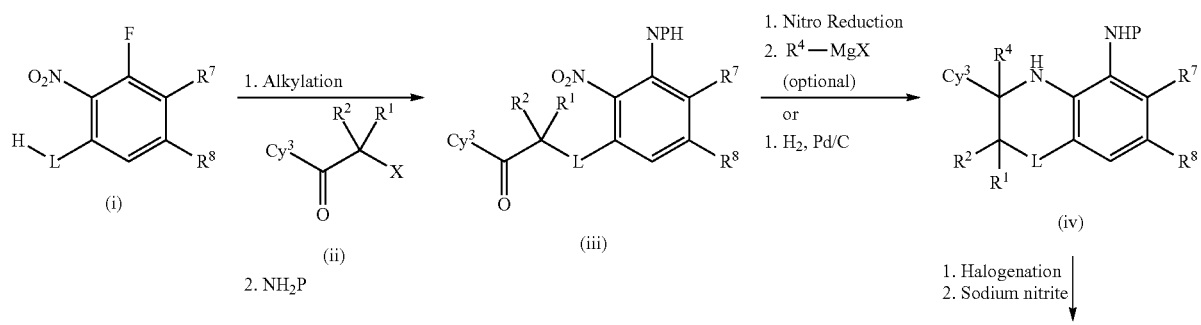

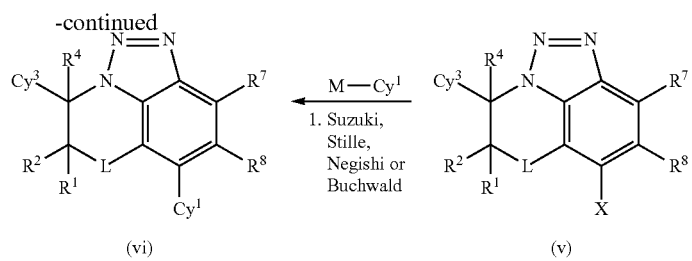

Compounds of Formula (I) can be formed as shown in Scheme VI. The phenols (L=O) or thiols (L=S) (i) can be nitrated using standard conditions (HNO$_3$/H$_2$SO$_4$) and selectively reduced with tin chloride to give the aniline nitro compound which can be alkylated using standard alkylating conditions with Cy$^3$COC(R$^1$R$^2$)—X (ii) (X=leaving group, such as halo (Br, Cl, or I) or mesylate) or Mitsunobu conditions (e.g., Cy$^3$COC(R$^1$R$^2$)—X (ii) (X=OH), DEAD, Ph$_3$P) to afford ether derivatives (iii). Cyclization in situ or upon heating can afford aminol (iv). Reduction of the nitro compound (iv) with iron can give, after in situ dehydration, the aniline (v). The halo group of (v) can be coupled to M-Cy$^1$, where M is a boronic acid, boronic ester or an appropriately substituted metal (e.g., Cy$^1$-M is Cy$^1$-B(OH)$_2$, Cy$^1$-Sn(Bu)$_4$, or Zn—Cy$^1$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give compounds (vi). Alternatively, M-Cy$^1$ can be an amine containing heterocycle (where M is H and is attached to the amine nitrogen of the heterocycle Cy$^1$) with coupling to compound (v) being performed by heating with a base or under Buchwald conditions (e.g., in the presence of a palladium(0) catalyst, such as tetrakis(triphenylphosphine)palladium(0) and a base (e.g., an alkoxide base)) to give compounds (vi). Reduction of imine (vi) (e.g., sodium borohydride or Pd/H$_2$) followed by treatment with sodium nitrite can give derivatives of Formula (I) (vii).

Scheme VI

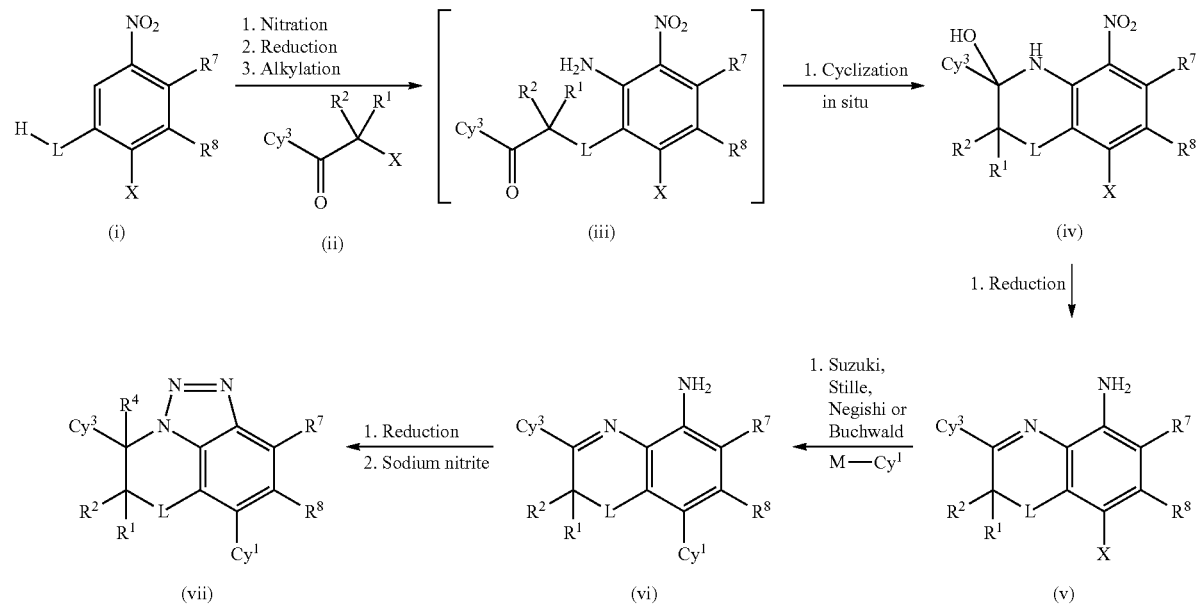

Halo-ketone intermediates (ii) from Schemes I, IV, V, and VI can be synthesized as shown in Scheme VII. The carboxylic acid (i) can be activated with a coupling agent (e.g., HBTU, HATU or EDC) and then reacted with N, O-dimethylhydroxylamine to give a N-methoxy-N-methylcarboxamide derivative (ii). Amide (ii) may then be reacted with a Grignard reagent of formula R$^1$R$^2$—CH—MgX$^1$ (X$^1$=halo) to give a ketone (iii) which can be halogenated with Br$_2$ or NXS (X=Br, Cl or I) to give halo-ketone (iv). The halo-ketone (iv) can be transformed using similar methods as shown in Schemes I, IV, V, and VI to afford compounds of Formula (I).

Scheme VII

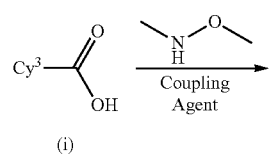

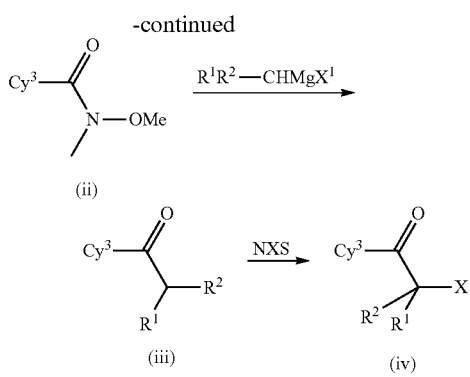

Compounds of Formula (I) can be formed as shown in Scheme VIII. The halo group of quinoline (i) can be coupled to M-Cy$^3$, where M is a boronic acid, boronic ester or an appropriately substituted metal (e.g., Cy$^3$-M is Cy$^3$-B(OH)$_2$, Cy$^3$-Sn(Bu)$_4$, or Zn—Cy$^3$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give compounds (ii). Reduction of quinoline (ii) (e.g., Hantzsch ester/diphenyl hydrogen phosphate or borane-pyridine complex/acetic acid) can give tetrahydroquinoline (iii). Treatment of the aniline of (iii) with sodium nitrite can give nitroso compound (iv). Reduction of nitroso (iv) (e.g., sodium dithionite, zinc with acetic acid, or zinc with saturated aqueous ammonium chloride) gives the hydrazine which can cyclize (in situ or with heat) with the adjacent ester to give tricyclic compounds (v). Compounds (v) can be halogenated with N-chlorosuccinimide, N-bromosuccinimide or N-iodosuccinimide to give halide (vi) where X=Cl, Br or I. The halo group of (vi) can be coupled to M-Cy$^1$, where M is a boronic acid, boronic ester or an appropriately substituted metal (e.g., Cy$^1$-M is Cy$^1$-B(OH)$_2$, Cy$^1$-Sn(Bu)$_4$, or Zn—Cy$^1$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of Formula (I) (vii). Alternatively, M-Cy$^1$ can be an amine containing heterocycle (where M is H and is attached to the amine nitrogen of the heterocycle Cy$^1$) with coupling to compound (vi) being performed by heating with a base or under Buchwald conditions (e.g., in the presence of a palladium(0) catalyst, such as tetrakis(triphenylphosphine) palladium(0) and a base (e.g., an alkoxide base)) to give a derivative of Formula (I) (vii). Compound (vii) can be alkylated (e.g., alkyl halide and a base, such as triethylamine, NaH or Na$_2$CO$_3$; or under Mitsunobu conditions) to afford the N-substituted derivatives of Formula (I) (viii) or O-substituted derivatives of Formula (I) (ix) (R$^6$=OR$^{6B}$).

Scheme VIII

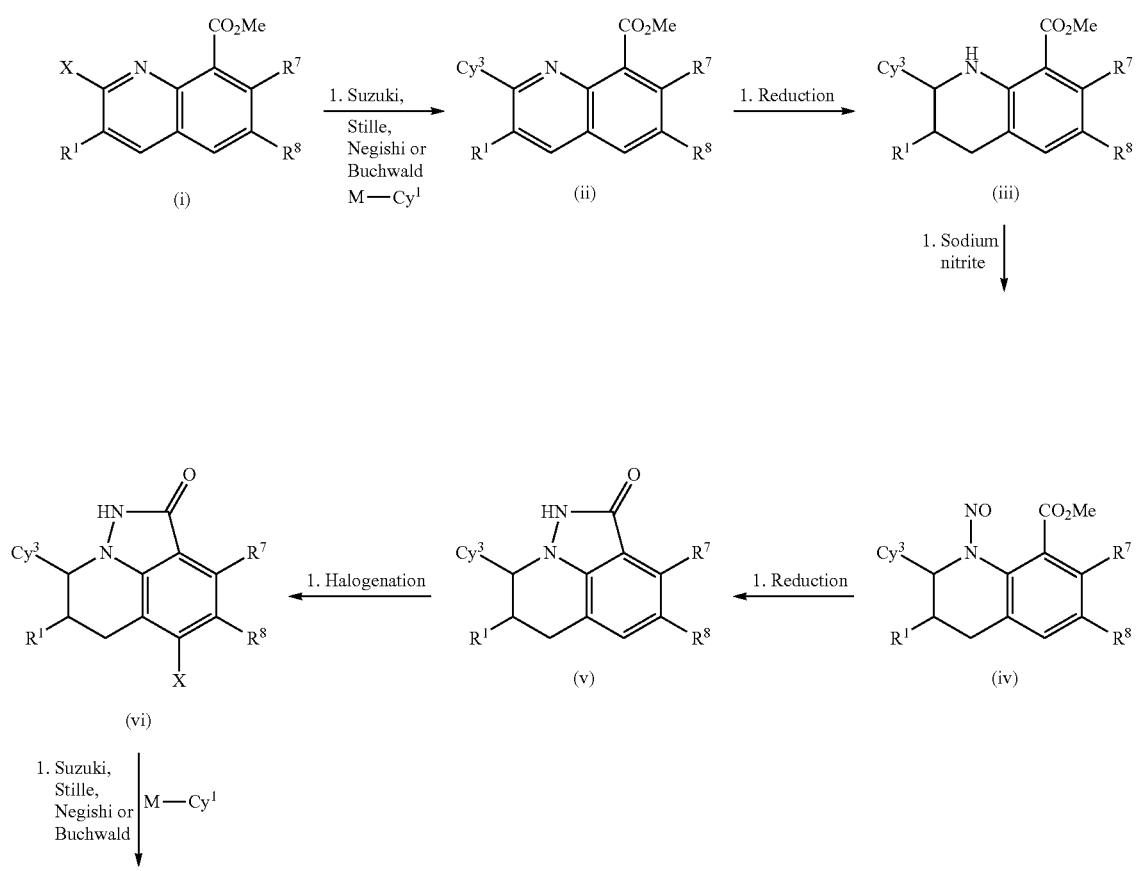

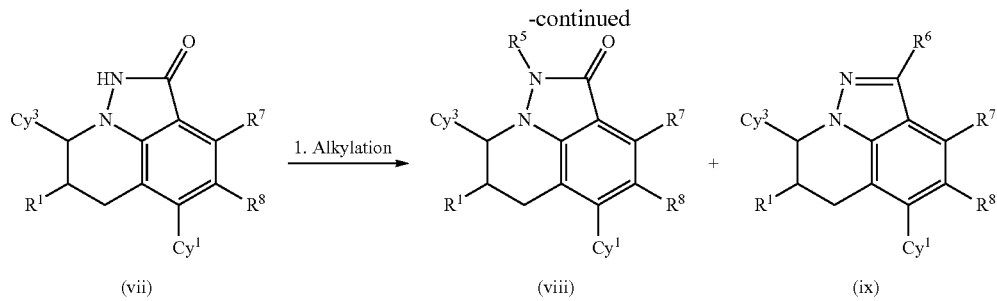

Compounds of Formula (I) can be formed as shown in Scheme IX. Aniline (i) can be reacted with aldehyde of formula —OHCC(R$^1$)=CHCy$^3$ (ii), to give quinoline derivatives (iii). Ester (iii) can then be converted to compounds of Formula (I) by similar methods for ester (ii) shown in Scheme VIII.

Scheme IX

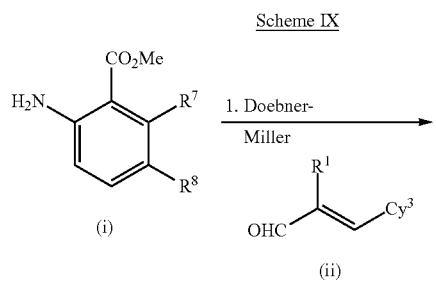

Compounds of Formula (I) can be formed as shown in Scheme X. The sulfide (i) can be reacted with an oxidant, such as mCPBA or H$_2$O$_2$ or dioxirane, to give the sulfoxide (ii) which can be further oxidized with an oxidant, such as mCPBA or H$_2$O$_2$ or dioxirane, to give the sulfone (iii).

Scheme X

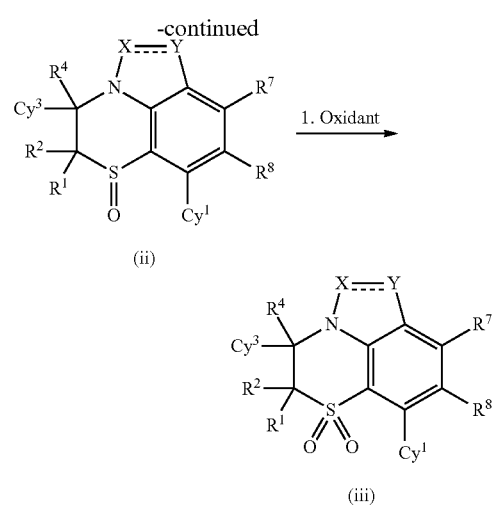

Compounds of Formula (I) can be formed as shown in Scheme XI. The carbonyl of tricyclic (i) can be converted to the thiocarbonyl with Lawesson's reagent to give compounds of Formula (I) (ii).

Scheme XI

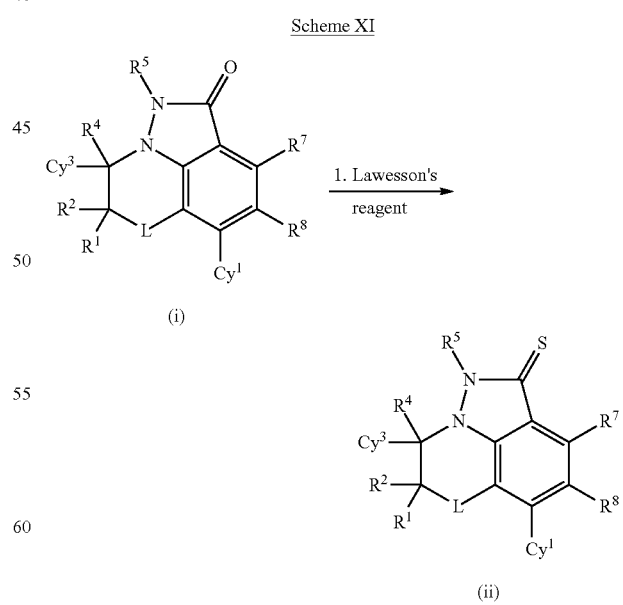

For the synthesis of particular compounds, the general schemes described above can be modified. For example, the products or intermediates can be modified to introduce particular functional groups. Alternatively, the substituents can be modified at any step of the overall synthesis by methods known to one skilled in the art, e.g., as described by Larock, *Comprehensive Organic Transformations: A Guide to Functional Group Preparations* (Wiley, 1999); and Katritzky et al. (Ed.), *Comprehensive Organic Functional Group Transformations* (Pergamon Press 1996).

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

III. Uses of the Compounds

Compounds of the invention are BET protein inhibitors and, thus, are useful in treating diseases and disorders associated with activity of BET proteins. For the uses described herein, any of the compounds of the invention, including any of the embodiments thereof, may be used.

The compounds of the invention can inhibit one or more of BET proteins BRD2, BRD3, BRD4, and BRD-t. In some embodiments, the compounds of the invention selectively inhibit one or more BET proteins over another. "Selective" means that the compound binds to or inhibits a BET protein with greater affinity or potency, respectively, compared to a reference, such as another BET protein. For example, the compounds can be selective for BRD2 over BRD3, BRD4 and BRD-t, selective for BRD3 over BRD2, BRD4 and BRD-t, selective for BRD4 over BRD2, BRD3 and BRD-t, or selective for BRD-t over BRD2, BRD3 and BRD4. In some embodiments, the compounds inhibit two or more of the BET proteins, or all of the BET proteins. In general, selectivity can be at least about 5-fold, at least about 10-fold, at least about 20-fold, at least about 50-fold, at least about 100-fold, at least about 200-fold, at least about 500-fold or at least about 1000-fold.

The compounds of the invention are therefore useful for treating BET protein mediated disorders. The term "BET-mediated" refers to any disease or condition in which one or more of the BET proteins, such as BRD2, BRD3, BRD4 and/or BRD-t, or a mutant thereof, plays a role, or where the disease or condition is associated with expression or activity of one or more of the BET proteins. The compounds of the invention can therefore be used to treat or lessen the severity of diseases and conditions where BET proteins, such as BRD2, BRD3, BRD4, and/or BRD-t, or a mutant thereof, are known to play a role.

Diseases and conditions treatable using the compounds of the invention include, but are not limited to, cancer and other proliferative disorders, autoimmune disease, chronic inflammatory diseases, acute inflammatory diseases, sepsis, and viral infection. The diseases can be treated by administering to an individual (e.g., a patient) in need of the treatment a therapeutically effective amount or dose of a compound of the invention, or any of the embodiments thereof, or a pharmaceutical composition thereof. The present disclosure also provides a compound of the invention, or any of the embodiments thereof, or a pharmaceutical composition thereof, for use in treating a BET-mediated disease or disorder. Also provided is the use of a compound of the invention, or any of the embodiments thereof, or a pharmaceutical composition thereof, in the manufacture of a medicament for treating a BET-mediated disease or disorder.

Diseases that can be treated with the compounds of the invention include cancers. The cancers can include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor. In some embodiments, the cancer can be adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor.

The diseases treatable using the compounds of the invention also include MYC dependent cancers wherein the cancer is associated with at least one of myc RNA expression or MYC protein expression. A patient can be identified for such treatment by determining myc RNA expression or MYC protein expression in the cancerous tissue or cells.

Diseases that can be treated with compounds of the invention also include non-cancerous proliferative disorders. Examples of proliferative disorders that can be treated include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

The diseases and conditions that can be treated with the compounds of the invention also include chronic autoimmune and inflammatory conditions. Examples of autoimmune and inflammatory conditions that can be treated include acute, hyperacute or chronic rejection of transplanted organs, acute gout, acute inflammatory responses (such as acute respiratory distress syndrome and ischemia/reperfusion injury), Addison's disease, agammaglobulinemia, allergic rhinitis, allergy, alopecia, Alzheimer's disease, appendicitis, atherosclerosis, asthma, osteoarthritis, juvenile arthritis, psoriatic arthritis, rheumatoid arthriti, satopic dermatitis, autoimmune alopecia, autoimmune hemolytic and thrombocytopenic states, autoimmune hypopituitarism, autoimmune polyglandular disease, Behcet's disease, bullous skin diseases, cholecystitis, chronic idiopathic thrombocytopenic purpura, chronic obstructive pulmonary disease (COPD), cirrhosis, degenerative joint disease, depression, dermatitis, dermatomyositis, eczema, enteritis, encephalitis, gastritis glomerulonephritis, giant cell arteritis, Goodpasture's syndrome, Guillain-Barre syndrome, gingivitis, Graves' disease, Hashimoto's thyroiditis, hepatitis, hypophysitis, inflammatory bowel disease (Crohn's disease and ulcerative colitis), inflammatory pelvic disease, irritable bowel syndrome, Kawasaki disease, LPS-induced endotoxic shock, meningitis, multiple sclerosis, myocarditis, myasthenia gravis, mycosis fungoides, myositis, nephritis, osteomyelitis, pancreatitis, Parkinson's disease, pericarditis, pernicious anemia, pneumonitis, primary biliary sclerosing cholangitis, polyarteritis nodosa, psoriasis, retinitis, scleritis, scleracierma, scleroderma, sinusitis, Sjogren's disease, sepsis, septic shock, sunburn, systemic lupus erythematosus, tissue graft rejection, thyroiditis, type I diabetes, Takayasu's arteritis, urethritis, uveitis, vasculitis, vasculitis including giant cell arteritis, vasculitis with organ involvement such as glomerulonephritis, vitiligo, Waldenstrom macroglobulinemia and Wegener's granulomatosis.

The diseases and conditions that can be treated with the compounds of the invention also include diseases and conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

Other diseases that can be treated with the compounds of the invention include viral infections. Examples of viral infections that can be treated include Epstein-Barr virus, hepatitis B virus, hepatitis C virus, herpes virus, human immunodeficiency virus, human papilloma virus, adenovirus, poxvirus and other episome-based DNA viruses. The compounds can therefore be used to treat disease and conditions such as herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus. In one particular embodiment, the compounds of the invention are indicated for the treatment of human papilloma virus infections of skin or cervical epithelia.

The diseases and conditions that can be treated with the compounds of the invention also include conditions that are associated with ischaemia-reperfusion injury. Examples of such conditions include, but are not limited to conditions such as myocardial infarction, cerebrovascular ischaemia (stroke), acute coronary syndromes, renal reperfusion injury, organ transplantation, coronary artery bypass grafting, cardio-pulmonary bypass procedures and pulmonary, renal, hepatic, gastro-intestinal or peripheral limb embolism.

The compounds of the invention are also useful in the treatment of disorders of lipid metabolism via the regulation of APO-A1 such as hypercholesterolemia, atherosclerosis and Alzheimer's disease.

The compounds of the invention are also useful in the treatment of fibrotic conditions such as idiopathic pulmonary fibrosis, renal fibrosis, post-operative stricture, keloid formation, scleroderma and cardiac fibrosis.

The compounds of the invention can also be used to treat ophthamological indications such as dry eye.

As used herein, the term "contacting" refers to the bringing together of indicated moieties in an in vitro system or an in vivo system. For example, "contacting" a BET protein with a compound of the invention includes the administration of a compound of the present invention to an individual or patient, such as a human, having a BET protein, as well as, for example, introducing a compound of the invention into a sample containing a cellular or purified preparation containing the BET protein.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

The compounds of the invention can be used in combination treatments where the compound of the invention is administered in conjunction with other treatments such as the administration of one or more additional therapeutic agents. The additional therapeutic agents are typically those which are normally used to treat the particular condition to be treated. The additional therapeutic agents can include, e.g., chemotherapeutics, anti-inflammatory agents, steroids, immunosuppressants, as well as Bcr-Abl, Flt-3, RAF, FAK, and JAK kinase inhibitors for treatment of BET protein-associated diseases, disorders or conditions. The one or more additional pharmaceutical agents can be administered to a patient simultaneously or sequentially.

In some embodiments, the compounds of the invention can be used in combination with a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, the compounds of the invention can be used in combination with chemotherapeutic agents, or other anti-proliferative agents. The compounds of the invention can also be used in combination with medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, do farabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

For treating cancer and other proliferative diseases, the compounds of the invention can be used in combination with ruxolitinib.

For treating autoimmune or inflammatory conditions, the compound of the invention can be administered in combination with a corticosteroid such as triamcinolone, dexamethasone, fluocinolone, cortisone, prednisolone, or flumetholone.

For treating autoimmune or inflammatory conditions, the compound of the invention can be administered in combination with an immune suppressant such as fluocinolone acetonide (Retisert®), rimexolone (AL-2178, Vexol, Alcon), or cyclosporine (Restasis®).

For treating autoimmune or inflammatory conditions, the compound of the invention can be administered in combination with one or more additional agents selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino] purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, the compound of the invention can be administered in combination with one or more agents selected from an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Other examples of agents, one or more of which a provided compound may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, such as dexamethasone or prednisone, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

IV. Formulation, Dosage Forms and Administration

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1,000 mg (1 g), more usually about 100 mg to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions of the invention contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions of the invention contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% Aviv of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

V. Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating BET proteins in tissue samples, including human, and for identifying BET protein ligands by inhibition binding of a labeled compound. Accordingly, the present invention includes BET protein assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$. The radionuclide that is incorporated in the instant radio-labeled compounds will depend on the specific application of that radio-labeled compound. For example, for in vitro BET protein labeling and competition assays, compounds that incorporate $^{3}H$, $^{14}C$, $^{82}Br$, $^{125}I$, $^{131}I$, or $^{35}S$ will generally be most useful. For radio-imaging applications $^{11}C$, $^{18}F$, $^{125}I$, $^{124}I$, $^{131}I$, $^{75}Br$, $^{76}Br$ or $^{77}Br$ will generally be most useful.

It is to be understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a BET protein by monitoring its concentration variation when contacting with the BET protein, through tracking of the labeling. For example, a test compound (labeled) can be evaluated for its ability to reduce binding of another compound which is known to bind to a BET protein (i.e., standard compound). Accordingly, the ability of a test compound to compete with the standard compound for binding to the BET protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

VI. Kits

The present invention also includes pharmaceutical kits useful, for example, in the treatment or prevention of BET protein-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of one or more BET proteins as described below.

EXAMPLES

Example 1

9-(3,5-Dimethylisoxazol-4-yl)-3-phenyl-2,3-dihydro[1,4]oxazino[2,3,4-hi]indazol-6(5H)-one

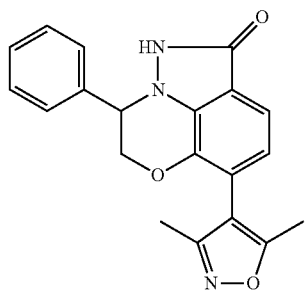 [SMILES: Cc1noc(C)c1-c1ccc2c(=O)[nH]n3c2c1OCC3c1ccccc1]

Step 1. Methyl 4-bromo-3-hydroxy-2-nitrobenzoate

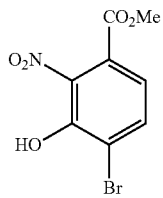 [SMILES: COC(=O)c1ccc(Br)c(O)c1[N+](=O)[O-]]

A solution of 4-bromo-3-hydroxybenzoic acid (6.00 g, 27.6 mmol) [Combi Blocks, CA-4188] in sulfuric acid (138 mL) was stirred at 20° C. for 30 min, cooled to 0° C., and treated with a chilled (cooled with ice bath) solution of fuming nitric acid (1.39 mL, 33.2 mmol)/sulfuric acid (69.1 mL) dropwise. The reaction mixture was stirred at 0° C. for 30 min, quenched by pouring over ice, and extracted with ethyl acetate (2×250 mL). The combined organic extracts were washed with brine, dried over sodium sulfate, filtered, and concentrated to give the desired nitro intermediate (7.41 g, >100%) that was used without further purification. LCMS calculated for $C_7H_8BrN_2O_5$ $(M+NH_4)^+$: m/z=279.0, 281.0. found: 279.0, 280.9.

The crude nitro intermediate was dissolved in methanol (110 mL), cooled to 0° C. and treated with thionyl chloride (9.08 mL, 124 mmol) dropwise. After addition the ice bath was removed and after warming to ambient temperature the solution was heated at 70° C. for 16 h. The reaction mixture was concentrated to a tan solid. Purification by flash column chromatography (100% hexanes to 70% EtOAc [containing 5% methanol]/30% hexanes) gave the desired product (5.41 g, 71%) as a tan solid. LCMS calculated for $C_8H_{10}BrN_2O_5$ $(M+NH_4)^+$: m/z=293.0, 295.0. found: 293.0, 294.9.

Step 2. Methyl 3-(benzyloxy)-4-bromo-2-nitrobenzoate

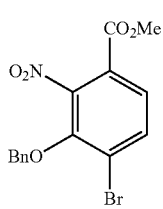

A solution of methyl 4-bromo-3-hydroxy-2-nitrobenzoate (5.41 g, 19.6 mmol) and potassium carbonate (5.42 g, 39.2 mmol) in N,N-dimethylformamide (30 mL, 387 mmol) was treated with benzyl bromide (3.26 mL, 27.4 mmol) and stirred at 60° C. for 1 h. The reaction mixture was diluted with water (250 mL) and extracted with ethyl acetate (2×150 mL). The combined organic extracts were washed with brine, dried over sodium sulfate, filtered, and concentrated to give a crude tan oil. Purification by flash column chromatography (100% hexanes to 50% EtOAc/hexanes) gave the desired product (6.99 g, 97%) as a yellow solid. LCMS calculated for $C_{15}H_{16}BrN_2O_5$ $(M+NH_4)^+$: m/z=383.0, 385.0. found: 383.0, 385.0.

Step 3. Methyl 3-(benzyloxy)-4-(3,5-dimethylisoxazol-4-yl)-2-nitrobenzoate and methyl 4-(3,5-dimethylisoxazol-4-yl)-3-hydroxy-2-nitrobenzoate

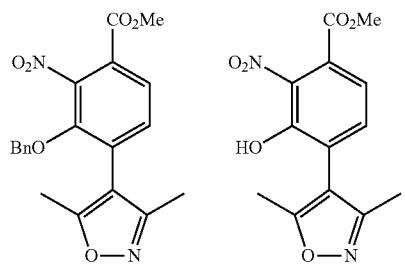 [SMILES: COC(=O)c1ccc(-c2c(C)noc2C)c(OCc2ccccc2)c1[N+](=O)[O-] ; COC(=O)c1ccc(-c2c(C)noc2C)c(O)c1[N+](=O)[O-]]

A mixture of methyl 3-(benzyloxy)-4-bromo-2-nitrobenzoate (6.49 g, 17.7 mmol), (3,5-dimethylisoxazol-4-yl)boronic acid (6.24 g, 44.3 mmol) [Matrix Scientific, 004078], and potassium carbonate (9.80 g, 70.9 mmol) in 1,4-dioxane (69.5 mL) and water (34.8 mL) was degassed with nitrogen for 10 min. The reaction mixture was treated with [1,1'-bis(diphenylphosphino)ferrocene]dichloropalladium(II) complexed with dichloromethane (1:1) (1.45 g, 1.77 mmol), degassed with nitrogen for another 5 min, and heated at 80° C. for 1 h. The reaction mixture was filtered through Celite and the solids washed with EtOAc (200 mL). The filtrated was washed with water (200 mL), brine (100 mL), dried over sodium sulfate, filtered, and concentrated to give a brown oil. The aqueous layer from the first 200 mL wash contained the desired product that had lost the benzyl group. This was cooled to 0° C., acidified with 6 M HCl, and extracted with EtOAc (100 mL) to provide a brown oil. The two products were purified separately. Purification of the first batch by flash column chromatography (100% hexanes to 50% EtOAc [containing 5% methanol]/50% hexanes) gave the desired product, methyl 3-(benzyloxy)-4-(3,5-dimethylisoxazol-4-yl)-2-nitrobenzoate, (5.13 g, 76%) as a yellow solid. LCMS calculated for $C_{20}H_{19}N_2O_6$ $(M+H)^+$: m/z=383.1. found: 383.1. Purification of the second batch by flash column chromatography (100% hexanes to 80% EtOAc [containing 5% methanol]/20% hexanes) gave the desired product minus the benzyl group, methyl 4-(3,5-dimethylisoxazol-4-yl)-3-hydroxy-2-nitrobenzoate, (0.63 g, 12%) as a white solid. LCMS calculated for $C_{13}H_{13}N_2O_6$ $(M+H)^+$: m/z=293.1. found: 293.0.

Step 4. Methyl 2-amino-4-(3,5-dimethylisoxazol-4-yl)-3-hydroxybenzoate

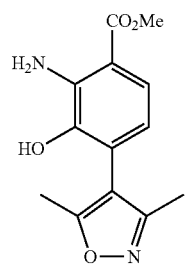 [SMILES: COC(=O)c1ccc(-c2c(C)noc2C)c(O)c1N]

A suspension of methyl 3-(benzyloxy)-4-(3,5-dimethyl-isoxazol-4-yl)-2-nitrobenzoate (0.959 g, 2.51 mmol) in methanol (49.9 mL) was degassed with nitrogen, treated with 10% Pd/C, Degussa type, (0.144 g), and hydrogenated with a balloon of hydrogen for 1 h. A solution formed during the first 30 min. The reaction mixture was filtered through a cartridge and the solids were washed with methanol. The filtrate was concentrated to give the desired product (0.656 g, quantitative) as an orange solid that was used without further purification. LCMS calculated for $C_{13}H_{15}N_2O_4$ $(M+H)^+$: m/z=263.1. found: 263.1.

Alternatively, methyl 4-(3,5-dimethylisoxazol-4-yl)-3-hydroxy-2-nitrobenzoate, from Step 3, can be treated in the same fashion to give methyl 2-amino-4-(3,5-dimethylisoxazol-4-yl)-3-hydroxybenzoate in quantitative yield.

Step 5. Methyl 8-(3,5-dimethylisoxazol-4-yl)-3-phenyl-3,4-dihydro-2H-1,4-benzoxazine-5-carboxylate

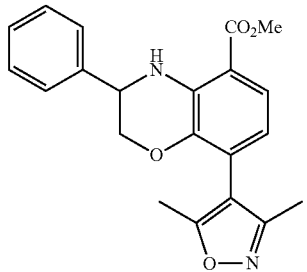 [SMILES: COC(=O)c1ccc(-c2c(C)noc2C)c2c1NC(c1ccccc1)CO2]

A solution of methyl 2-amino-4-(3,5-dimethylisoxazol-4-yl)-3-hydroxybenzoate (0.656 g, 2.50 mmol) and potassium carbonate (0.691 g, 5.00 mmol) in N,N-dimethylformamide (7.5 mL) was treated with 2-bromoacetophenone (0.572 g, 2.88 mmol) and stirred for 30 min. The reaction mixture was poured into water (100 mL) and extracted with ethyl acetate (100 mL). The organic layer was separated, washed with brine, dried over sodium sulfate, filtered, and concentrated to give the intermediate imine as a tan foam that was used without further purification. The crude intermediate imine was dissolved in methanol (25 mL) and treated with acetic acid (0.284 mL, 5.00 mmol). The solution was degassed with nitrogen, treated with 10% Pd/C, Degussa type, (0.131 g), and hydrogenated with a balloon of hydrogen for 1 h. Due to incomplete reaction, the mixture was treated with additional 10% Pd/C, Degussa type, (0.066 g) and hydrogenated with a balloon of hydrogen for another 1 h. The reaction mixture was filtered through a cartridge and the solids were washed with methanol, ethyl acetate, and dichloromethane. The filtrate was concentrated to give the crude product. Purification by flash column chromatography (100% hexanes to 60% EtOAc/hexanes) gave the desired product (0.661 g, 73%) as a yellow solid. LCMS calculated for $C_{21}H_{21}N_2O_4$ $(M+H)^+$: m/z=365.1. found: 365.1.

Step 6. Methyl 8-(3,5-dimethylisoxazol-4-yl)-4-nitroso-3-phenyl-3,4-dihydro-2H-1,4-benzoxazine-5-carboxylate

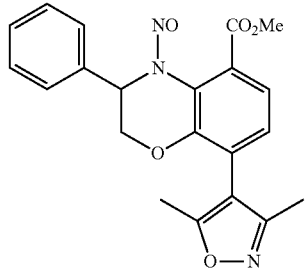

A suspension of methyl 8-(3,5-dimethylisoxazol-4-yl)-3-phenyl-3,4-dihydro-2H-1,4-benzoxazine-5-carboxylate (0.230 g, 0.631 mmol) in ethyl acetate (6.13 mL) was cooled to 0° C. and treated with 6.0 M hydrogen chloride in water (0.789 mL, 4.73 mmol) and water (0.460 mL) followed by sodium nitrite (0.0871 g, 1.26 mmol) in water (0.690 mL) dropwise. The reaction mixture was stirred at 0° C. for 15 min, the ice bath was removed, and stirred for 30 min which gave a biphasic solution. After another 30 min a suspension was present. The reaction mixture was diluted with EtOAc (40 mL) and water (20 mL). The organic layer was washed with brine, dried over sodium sulfate, filtered, and concentrated to give a crude tan solid. Purification by flash column chromatography (100% hexanes to 50% EtOAc/hexanes) gave the desired product (0.228 g, 92%) as a yellow solid. LCMS calculated for $C_{21}H_{20}N_2O_4$ $([M-NO]+H)^+$: m/z=364.1. found: 364.1.

Step 7. 9-(3,5-Dimethylisoxazol-4-yl)-3-phenyl-2,3-dihydro[1,4]oxazino[2,3,4-hi]indazol-6(5H)-one A suspension of methyl 8-(3,5-dimethylisoxazol-4-yl)-4-nitroso-3-phenyl-3,4-dihydro-2H-1,4-benzoxazine-5-carboxylate (0.228 g, 0.580 mmol) in ethyl acetate (4.04 mL) and methanol (4.04 mL) at 0° C. was treated with saturated aqueous ammonium chloride solution (2.02 mL, 30.2 mmol) and then zinc (0.303 g, 4.64 mmol) was added in three portions over 6 min. The cooling bath was removed and the reaction mixture was stirred for 2 h. The reaction mixture was diluted with ethyl acetate (30 mL), filtered through a Celite pad, and rinsed with ethyl acetate (2×10 mL). The filtrate was washed with water (20 mL), brine, (20 mL), dried over sodium sulfate, filtered, and concentrated to give a crude tan foam. Purification by flash column chromatography (100% dichloromethane to 10% methanol/dichloromethane) gave the desired product (0.14 g, 70%) as a yellow foam. $^1$H NMR (500 MHz, DMSO-$d_6$) δ 10.98 (br s, 1H), 7.40-7.29 (m, 3H), 7.26 (d, J=8.3 Hz, 1H), 7.23-7.15 (m, 2H), 6.87 (d, J=8.2 Hz, 1H), 5.39 (br s, 1H), 4.74 (dd, J=11.5, 3.1 Hz, 1H), 4.61 (dd, J=11.5, 5.8 Hz, 1H), 2.31 (s, 3H), 2.15 (s, 3H). LCMS calculated for $C_{20}H_{18}N_3O_3$ $(M+H)^+$: m/z=348.1. found: 348.1.

Example 2

9-(3,5-Dimethylisoxazol-4-yl)-5-methyl-3-phenyl-2,3-dihydro[1,4]oxazino[2,3,4-hi]indazol-6(5H)-one and

Example 3

9-(3,5-Dimethylisoxazol-4-yl)-6-methoxy-3-phenyl-2,3-dihydro[1,4]oxazino[2,3,4-hi]indazole

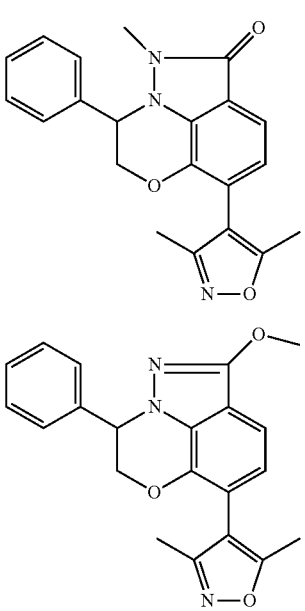

2

3

A solution of 9-(3,5-dimethylisoxazol-4-yl)-3-phenyl-2,3-dihydro[1,4]oxazino[2,3,4-hi]indazol-6(5H)-one (0.030 g, 0.086 mmol) in N,N-dimethylformamide (0.41 mL) was treated with sodium hydride (6.91 mg, 0.173 mmol) and stirred for 2 h. The reaction mixture was treated with methyl iodide (7.0 µL, 0.112 mmol) and stirred for 1 h. The reaction mixture was cooled to 0° C. and quenched with saturated ammonium chloride solution. The aqueous solution was extracted with ethyl acetate to give a crude tan solid. Purification via preparative LCMS (XBridge C18 column, eluting with a gradient of acetonitrile/water containing 0.1% trifluoroacetic acid, at flow rate of 30 mL/min) gave Example 2 (1.3 mg, 4%, first peak to elute) and Example 3 (2 mg, 6%, second peak to elute) (two separate passes through the preparative LCMS system was needed to isolate both peaks). Example 2: $^1$H NMR (500 MHz, CDCl$_3$) δ 7.48-7.39 (m, 4H), 7.37-7.30 (m, 2H), 6.97 (d, J=8.0 Hz, 1H), 4.74 (dd, J=11.9, 8.2 Hz, 1H), 4.55 (dd, J=12.0, 3.0 Hz, 1H), 4.34 (dd, J=8.1, 2.8 Hz, 1H), 2.95 (s, 3H), 2.35 (s, 3H), 2.23 (s, 3H); LCMS calculated for C$_{21}$H$_{20}$N$_3$O$_3$ (M+H)$^+$: m/z=362.1. found: 362.1. Example 3: 1H NMR (500 MHz, CDCl$_3$) δ 7.39-7.30 (m, 3H), 7.27 (d, J=8.3 Hz, 1H), 7.18-7.10 (m, 2H), 6.81 (d, J=8.3 Hz, 1H), 5.37 (dd, J=5.4, 3.4 Hz, 1H), 4.67 (dd, J=11.4, 3.4 Hz, 1H), 4.51 (dd, J=11.5, 5.5 Hz, 1H), 4.04 (s, 3H), 2.34 (s, 3H), 2.23 (s, 3H); LCMS calculated for C$_{21}$H$_{20}$N$_3$O$_3$ (M+H)$^+$: m/z=362.1. found: 362.1.

Example 4

9-(3,5-Dimethylisoxazol-4-yl)-3-phenyl-2,3-dihydro[1,4]oxazino[2,3,4-hi]indazole

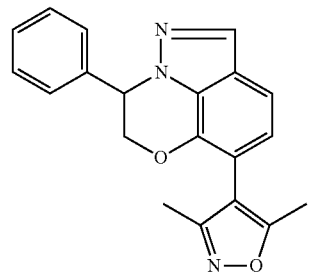

Step 1. [8-(3,5-Dimethylisoxazol-4-yl)-3-phenyl-3,4-dihydro-2H-1,4-benzoxazin-5-yl]methanol

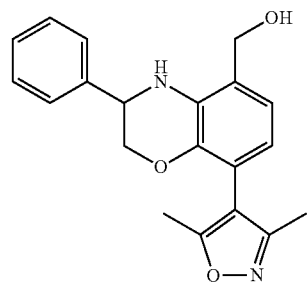 [SMILES: Cc1noc(C)c1-c1ccc(CO)c2c1OCC(c1ccccc1)N2]

A solution of methyl 8-(3,5-dimethylisoxazol-4-yl)-3-phenyl-3,4-dihydro-2H-1,4-benzoxazine-5-carboxylate (0.150 g, 0.412 mmol) in tetrahydrofuran (4.50 mL) at 0° C. was treated with 1.0 M lithium tetrahydroaluminate in THF (0.823 mL, 0.823 mmol) dropwise. After complete addition the mixture was stirred at 0° C. for 15 min. The reaction mixture was quenched with saturated ammonium chloride solution (20 mL), warmed to R.T., and extracted with ethyl acetate (2×20 mL). The combined organic extracts were dried over sodium sulfate, filtered, and concentrated to give a colorless residue. Purification by flash column chromatography (100% hexanes to 70% EtOAc [containing 5% methanol]/30% hexanes) gave the desired product (0.13 g, 94%) as a white foam. LCMS calculated for C$_{20}$H$_{21}$N$_2$O$_3$ (M+H)$^+$: m/z=337.2. found: 337.2.

Step 2. [4-Amino-8-(3,5-dimethylisoxazol-4-yl)-3-phenyl-3,4-dihydro-2H-1,4-benzoxazin-5-yl]methanol

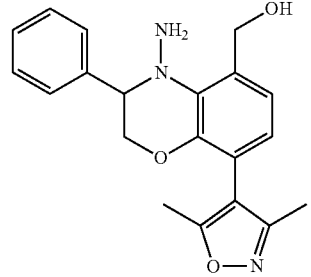 [SMILES: Cc1noc(C)c1-c1ccc(CO)c2c1OCC(c1ccccc1)N2N]

A solution of [8-(3,5-dimethylisoxazol-4-yl)-3-phenyl-3,4-dihydro-2H-1,4-benzoxazin-5-yl]methanol (0.129 g, 0.383 mmol) in ethyl acetate (2.79 mL) at 0° C. was treated with water (0.42 mL) and 6.0 M hydrogen chloride in water (0.479 mL, 2.88 mmol) followed by sodium nitrite (40 mg, 0.575 mmol) in water (0.28 mL). The reaction mixture was stirred at 0° C. for 30 min and diluted with ethyl acetate (30 mL) and water (20 mL). The organic layer was separated, washed with brine, dried over sodium sulfate, filtered, and concentrated to give the intermediate nitroso compound that was used immediately without further purification. The crude intermediate was dissolved in tetrahydrofuran (2.25 mL), cooled to 0° C., treated with 1.0 M lithium tetrahydroaluminate in THF (0.767 mL, 0.767 mmol), and stirred at 0° C. for 30 min. The reaction mixture was quenched with saturated ammonium chloride solution, warmed to R.T., and extracted with ethyl acetate (2×30 mL). The combined organic extracts were washed with brine, dried over sodium sulfate, filtered, and concentrated to give a tan foam. Purification by flash column chromatography (100% hexanes to 70% EtOAc [containing 5% methanol]/30% hexanes) gave the desired product (88 mg, 65%) as a tan foam. LCMS calculated for $C_{20}H_{22}N_3O_3$ (M+H)$^+$: m/z=352.2. found: 352.2.

Step 3. 9-(3,5-Dimethylisoxazol-4-yl)-3-phenyl-2,3-dihydro[1,4]oxazino[2,3,4-hi]indazole A solution of 2.0 M oxalyl chloride in methylene chloride (0.132 mL) at −78° C. was treated with methylene chloride (0.363 mL) followed by dimethyl sulfoxide (0.025 mL, 0.353 mmol) dropwise. The reaction mixture was stirred at −78° C. for 20 min and treated with a solution of [4-amino-8-(3,5-dimethylisoxazol-4-yl)-3-phenyl-3,4-dihydro-2H-1,4-benzoxazin-5-yl]methanol (0.062 g, 0.18 mmol) in methylene chloride (1.50 mL) dropwise. The reaction mixture was stirred at −78° C. for 1 h and treated with triethylamine (0.0984 mL, 0.706 mmol) dropwise. The reaction mixture was stirred at −78° C. for 1 h and warmed to 25° C. The reaction mixture was quenched with water (2 mL) and diluted with methylene chloride (30 mL) and saturated ammonium chloride solution (10 mL). The organic layer was separated, washed with brine, dried over sodium sulfate, filtered, and concentrated to give a tan foam. Purification via preparative LCMS (XBridge C18 column, eluting with a gradient of acetonitrile/water containing 0.1% trifluoroacetic acid, at flow rate of 60 mL/min) gave the desired product (19 mg, 32%). $^1$H NMR (300 MHz, DMSO-d$_6$) δ 8.13 (s, 1H), 7.43 (d, J=8.3 Hz, 1H), 7.39-7.30 (m, 3H), 7.13-7.06 (m, 2H), 7.03 (d, J=8.3 Hz, 1H), 5.90 (dd, J=3.9 Hz, 1H), 4.79 (dd, J=11.6, 3.4 Hz, 1H), 4.69 (dd, J=11.6, 4.6 Hz, 1H), 2.32 (s, 3H), 2.16 (s, 3H). LCMS calculated for $C_{20}H_{18}N_3O_2$ (M+H)$^+$: m/z=332.1. found: 332.1.

Example 5

9-(3,5-Dimethylisoxazol-4-yl)-3-pyridin-2-yl-2,3-dihydro[1,4]oxazino[2,3,4-hi]indazol-6(5H)-one

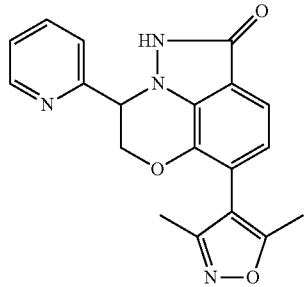 [SMILES: Cc1noc(C)c1-c1ccc2c(=O)[nH]n3c2c1OCC3c1ccccn1]

Example 5 was made according to the procedure of Example 1 using 2-bromo-1-pyridin-2-ylethanone hydrobromide instead of 2-bromoacetophenone in Step 5. $^1$H NMR (300 MHz, DMSO-d$_6$) δ 11.06 (br s, 1H), 8.56 (d, J=4.7 Hz, 1H), 7.82-7.69 (m, 1H), 7.33 (dd, J=7.1, 5.1 Hz, 1H), 7.28 (d, J=8.3 Hz, 1H), 6.86 (d, J=8.3 Hz, 2H), 5.52 (br s, 1H), 4.81 (d, J=3.6 Hz, 2H), 2.28 (s, 3H), 2.12 (s, 3H); LCMS calculated for $C_{19}H_{17}N_4O_3$ (M+H)$^+$: m/z=349.1. found: 349.1.

Example 6

9-(3,5-Dimethylisoxazol-4-yl)-5-methyl-3-pyridin-2-yl-2,3-dihydro[1,4]oxazino[2,3,4-hi]indazol-6(5H)-one and Example 7

9-(3,5-Dimethylisoxazol-4-yl)-6-methoxy-3-pyridin-2-yl-2,3-dihydro[1,4]oxazino[2,3,4-hi]indazole

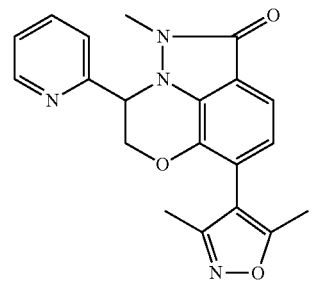

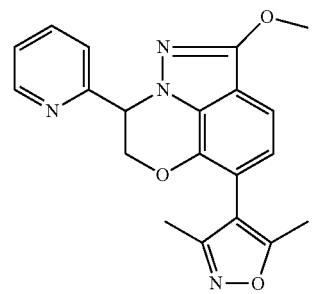

A solution of 9-(3,5-dimethylisoxazol-4-yl)-3-pyridin-2-yl-2,3-dihydro[1,4]oxazino[2,3,4-hi]indazol-6(5H)-one (0.03 g, 0.086 mmol) in N,N-dimethylformamide (0.24 mL) at 0° C. was treated with potassium carbonate (0.024 g, 0.172 mmol) followed by dropwise addition of 0.2 M methyl iodide in N,N-dimethylformamide (0.517 mL, 0.103 mmol) and stirred at 0° C. for 30 min. The ice bath was removed and the reaction mixture was stirred for 1 h. The reaction mixture was treated with water (20 mL) and extracted with EtOAc (30 mL). The organic layer was separated and washed with brine (10 mL), dried over sodium sulfate, filtered, and concentrated to give a colorless residue. Purification by preparative LCMS (XBridge C18 column, eluting with a gradient of acetonitrile/water containing 0.1% ammonium hydroxide, at flow rate of 30 mL/min) gave Example 6 (10 mg, 30%, first peak to elute) and Example 7 (8 mg, 20%, second peak to elute). Example 6: $^1$H NMR (500 MHz, DMSO-d$_6$) δ 8.47 (d, J=4.4 Hz, 1H), 7.86-7.71 (m, 1H), 7.38-7.29 (m, 1H), 7.29-7.21 (m, 2H), 7.00 (d, J=8.0 Hz, 1H), 5.14 (dd, J=3.4 Hz, 1H), 4.93 (d, J=3.5 Hz, 2H), 3.08 (s, 3H), 2.30 (s, 3H), 2.13 (s, 3H); LCMS calculated for C$_{20}$H$_{19}$N$_4$O$_3$ (M+H)$^+$: m/z=363.1. found: 363.1. Example 7: $^1$H NMR (500 MHz, DMSO-d$_6$) δ 8.55 (d, J=4.1 Hz, 1H), 7.82-7.68 (m, 1H), 7.33 (dd, J=7.0, 5.2 Hz, 1H), 7.27 (d, J=8.3 Hz, 1H), 6.91 (d, J=8.3 Hz, 1H), 6.82 (d, J=7.9 Hz, 1H), 5.76-5.66 (m, 1H), 4.93-4.73 (m, 2H), 3.99 (s, 3H), 2.27 (s, 3H), 2.11 (s, 3H); LCMS calculated for C$_{20}$H$_{19}$N$_4$O$_3$ (M+H)$^+$: m/z=363.1. found: 363.1.

Example 8

9-(3,5-Dimethylisoxazol-4-yl)-3-pyridin-2-yl-2,3-dihydro[1,4]oxazino[2,3,4-hi]indazole trifluoroacetate

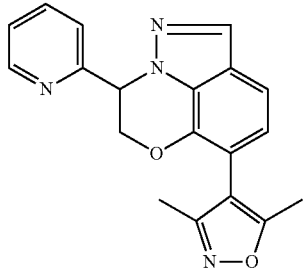 [SMILES: Cc1noc(C)c1-c1ccc2cnn3c2c1OCC3c1ccccn1]

The compound of Example 8 was made according to the procedure of Example 4 using methyl 8-(3,5-dimethylisoxazol-4-yl)-3-pyridin-2-yl-3,4-dihydro-2H-1,4-benzoxazine-5-carboxylate instead of 8-(3,5-dimethylisoxazol-4-yl)-3-phenyl-3,4-dihydro-2H-1,4-benzoxazine-5-carboxylate in Step 1. $^1$H NMR (400 MHz, DMSO-d$_6$) δ 8.55 (d, J=4.2 Hz, 1H), 8.17 (s, 1H), 7.79-7.71 (m, 1H), 7.43 (d, J=8.3 Hz, 1H), 7.34 (dd, J=6.9, 4.9 Hz, 1H), 7.02 (d, J=8.3 Hz, 1H), 6.77 (d, J=7.9 Hz, 1H), 6.05-5.97 (m, 1H), 4.92 (dd, J=11.5, 3.4 Hz, 1H), 4.82 (dd, J=11.5, 3.3 Hz, 1H), 2.29 (s, 3H), 2.13 (s, 3H); LCMS calculated for C$_{19}$H$_{17}$N$_4$O$_2$ (M+H)$^+$: m/z=333.1. found: 333.1.

Example 9

7-Bromo-9-(3,5-dimethylisoxazol-4-yl)-3-phenyl-2,3-dihydro[1,4]oxazino[2,3,4-hi]indazole

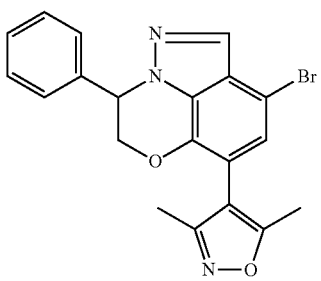 [SMILES: Cc1noc(C)c1-c1cc(Br)c2cnn3c2c1OCC3c1ccccc1]

A solution of 9-(3,5-dimethylisoxazol-4-yl)-3-phenyl-2,3-dihydro[1,4]oxazino[2,3,4-hi]indazole (0.011 g, 0.033 mmol) in acetonitrile (0.4 mL) at 0° C. was treated with N-bromosuccinimide (8.3 mg, 0.047 mmol) and stirred at 0° C. for 30 min. The reaction mixture was diluted with EtOAc (20 mL) and washed with saturated sodium bicarbonate solution (20 mL), dried over sodium sulfate, filtered, and concentrated to a colorless residue. Purification via preparative LCMS (XBridge C18 column, eluting with a gradient of acetonitrile/water containing 0.1% trifluoroacetic acid, at flow rate of 30 mL/min) gave desired product (9 mg, 70%). $^1$H NMR (300 MHz, DMSO-d$_6$) δ 8.11 (s, 1H), 7.40-7.32 (m, 3H), 7.28 (s, 1H), 7.16-7.05 (m, 2H), 5.99-5.89 (m, 1H), 4.81 (dd, J=11.7, 3.4 Hz, 1H), 4.71 (dd, J=11.6, 4.8 Hz, 1H), 2.32 (s, 3H), 2.16 (s, 3H); LCMS calculated for C$_{20}$H$_{17}$BrN$_3$O$_2$ (M+H)$^+$: m/z=410.0, 412.0. found: 410.0, 412.0.

Example 10

9-(3,5-Dimethylisoxazol-4-yl)-3-pyridin-3-yl-2,3-dihydro[1,4]oxazino[2,3,4-hi]indazol-6(5H)-one

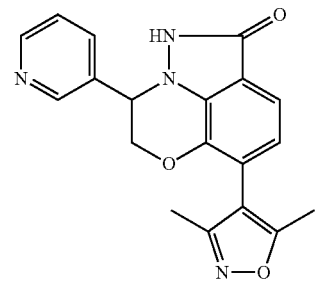 [SMILES: Cc1noc(C)c1-c1ccc2c(=O)[nH]n3c2c1OCC3c1cccnc1]

The compound of Example 10 was made according to the procedure of Example 1 using 2-bromo-1-pyridin-3-ylethanone hydrobromide instead of 2-bromoacetophenone in step 5. $^1$H NMR (400 MHz, DMSO-d$_6$) δ 8.65 (br s, 1H), 8.58 (br s, 1H), 7.78 (d, J=7.7 Hz, 1H), 7.58 (dd, J=7.6, 4.9 Hz, 1H), 7.29 (d, J=8.3 Hz, 1H), 6.91 (d, J=8.3 Hz, 1H), 5.48 (br s, 1H), 4.81 (dd, J=11.5, 3.3 Hz, 1H), 4.72 (dd, J=11.6, 6.0 Hz, 1H), 2.32 (s, 3H), 2.16 (s, 3H); LCMS calculated for C$_{19}$H$_{17}$N$_4$O$_3$ (M+H)$^+$: m/z=349.1. found: 349.1.

Example 11

9-(3,5-Dimethylisoxazol-4-yl)-5-methyl-3-pyridin-3-yl-2,3-dihydro[1,4]oxazino[2,3,4-hi]indazol-6(5H)-one and Example 12

9-(3,5-Dimethylisoxazol-4-yl)-6-methoxy-3-pyridin-3-yl-2,3-dihydro[1,4]oxazino[2,3,4-hi]indazole

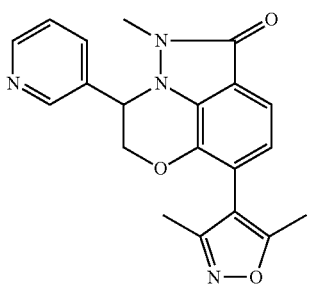

-continued

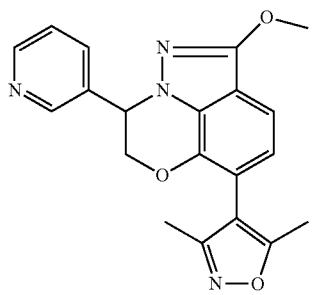

12

The compounds of Example 11 and Example 12 were made according to the procedure of Examples 6 and 7 using 9-(3,5-dimethylisoxazol-4-yl)-3-pyridin-3-yl-2,3-dihydro[1,4]oxazino[2,3,4-hi]indazol-6(5H)-one instead of 9-(3,5-dimethylisoxazol-4-yl)-3-pyridin-2-yl-2,3-dihydro[1, 4]oxazino[2,3,4-hi]indazol-6(5H)-one. Example 11 (first peak to elute): $^1$H NMR (400 MHz, DMSO-d$_6$) δ 8.56 (d, J=3.9 Hz, 1H), 8.51 (s, 1H), 7.61 (d, J=8.0 Hz, 1H), 7.40 (dd, J=7.8, 4.8 Hz, 1H), 7.31 (d, J=8.0 Hz, 1H), 7.09 (d, J=8.0 Hz, 1H), 5.08-4.98 (m, 1H), 4.96-4.84 (m, 2H), 3.01 (s, 3H), 2.33 (s, 3H), 2.16 (s, 3H); LCMS calculated for $C_{20}H_{19}N_4O_3$ (M+H)$^+$: m/z=363.1. found: 363.1. Example 12 (second peak to elute): $^1$H NMR (400 MHz, DMSO-d$_6$) δ 8.55 (d, J=3.8 Hz, 1H), 8.42 (s, 1H), 7.53 (d, J=8.0 Hz, 1H), 7.40 (dd, J=7.8, 4.8 Hz, 1H), 7.28 (d, J=8.3 Hz, 1H), 6.94 (d, J=8.3 Hz, 1H), 5.73-5.59 (m, 1H), 4.82 (dd, J=11.6, 3.2 Hz, 1H), 4.71 (dd, J=11.6, 5.1 Hz, 1H), 3.95 (s, 3H), 2.31 (s, 3H), 2.15 (s, 3H); LCMS calculated for $C_{20}H_{19}N_4O_3$ (M+H)$^+$: m/z=363.1. found: 363.1.

Example 13

7-(3,5-Dimethylisoxazol-4-yl)-9-fluoro-4-pyridin-3-yl-4,5-dihydro[1,2,3]triazolo[1,5,4-de][1,4]benzoxazine trifluoroacetate

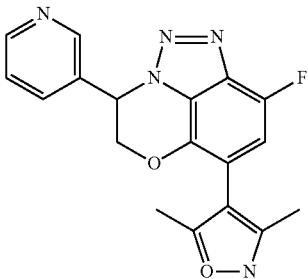

Step 1. 6-Bromo-4-fluoro-2,3-dinitrophenol

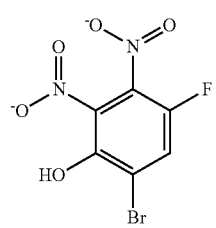

To a solution of 2-bromo-4-fluoro-5-nitrophenol (4.0 g, 17 mmol) (Ark # AK-27735) in methylene chloride (29.5 mL), 2.0 M nitric acid in methylene chloride (25 mL) was added and the mixture was stirred for 15 min at RT. The mixture was poured into ice-cold water and extracted with methylene chloride to give the crude product, 4.42 g, 93%.

Step 2. 2-Amino-6-bromo-4-fluoro-3-nitrophenol

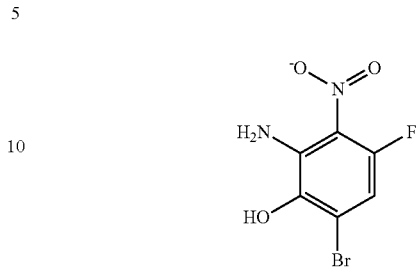

To a stirred solution of 6-bromo-4-fluoro-2,3-dinitrophenol (4.4 g, 16 mmol) in methanol (88 mL) and 12.0 M hydrogen chloride in water (40 mL) was added stannous chloride, dihydrate (11 g, 47 mmol). The reaction was stirred at RT for 15 min. Water was added and the mixture was extracted with ethyl acetate. The organic layer was separated and concentrated. Purification on silica gel using ethyl acetate in hexanes gave the desired compound, 2.48 g, 63%. $^1$H NMR (300 MHz, DMSO-d$_6$) δ 9.80 (br s, 3H), 6.80 (m, 1H).

Step 3. 8-Bromo-6-fluoro-5-nitro-3-pyridin-3-yl-3,4-dihydro-2H-1,4-benzoxazin-3-ol

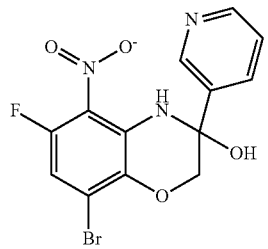

2-Amino-6-bromo-4-fluoro-3-nitrophenol (500 mg, 1.9 mmol) and potassium carbonate (780 mg, 5.7 mmol) were stirred in acetone (8 mL) for 5 minutes and 2-bromo-1-pyridin-3-ylethanone hydrobromide (530 mg, 1.9 mmol) was added as a solid over 5 minutes. The mixture was stirred at rt for 5 minutes and poured into water. The mixture was extracted with ethyl acetate. The extracts were washed with brine, dried over sodium sulfate, filtered and evaporated. Purification on silica gel using ethyl acetate in hexanes gave the desired compound, 0.69 g, 99%. LCMS calculated for $C_{13}H_{10}BrFN_3O_4$ (M+H)$^+$: m/z=370.1, 372.1. found: 370.0, 372.0.

Step 4. 8-Bromo-6-fluoro-3-pyridin-3-yl-2H-1,4-benzoxazin-5-amine

To 8-bromo-6-fluoro-5-nitro-3-pyridin-3-yl-3,4-dihydro-2H-1,4-benzoxazin-3-ol (690 mg, 1.9 mmol) in acetic acid (20 mL), iron (520 mg, 9.4 mmol) was added and heated at 60° C. overnight. The reaction was extracted with ethyl acetate to give the crude product, 0.60 g, 100%. $^1$H NMR (300 MHz, DMSO-$d_6$) δ 9.28 (s, 1H), 8.68 (m, 1H), 8.51 (m, 1H), 7.52 (m, 1H), 6.89 (m, 1H), 5.80 (s, 2H), 5.13 (s, 2H), 2.25 (s, 3H), 2.10 (s, 3H). LCMS calculated for $C_{13}H_{10}BrFN_3O$ $(M+H)^+$: m/z=322.0, 324.0. found: 321.8, 323.8.

Step 5. 8-(3,5-Dimethylisoxazol-4-yl)-6-fluoro-3-pyridin-3-yl-2H-1,4-benzoxazin-5-amine

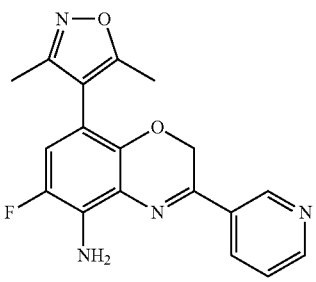 [SMILES: Cc1noc(C)c1-c1cc(F)c(N)c2c1OCC(c1cccnc1)=N2]

4-(Di-tert-butylphosphino)-N,N-dimethylaniline-dichloropalladium (2:1) (3.3 mg, 0.0047 mmol) and cesium fluoride (83 mg, 0.54 mmol), 8-bromo-6-fluoro-3-pyridin-3-yl-2H-1,4-benzoxazin-5-amine (50 mg, 0.2 mmol) and (3,5-dimethylisoxazol-4-yl)boronic acid (33 mg, 0.23 mmol) were stirred in 1-butanol (0.50 mL) and water (0.12 mL). The system was placed under vacuum and back-filled with nitrogen (repeated 3×) while stirring the suspension. The mixture was further degassed by bubbling nitrogen through the solution for 10 minutes. The mixture was heated at 100° C. for 1 hour. Extractive workup with ethyl acetate gave the desired compound 40 mg, 80%. $^1$H NMR (300 MHz, DMSO-$d_6$) δ 9.28 (s, 1H), 8.68 (m, 1H), 8.51 (m, 1H), 7.52 (m, 1H), 6.89 (m, 1H), 5.80 (s, 2H), 5.13 (s, 2H), 2.25 (s, 3H), 2.10 (s, 3H). LCMS calculated for $C_{18}H_{16}FN_4O_2$ $(M+H)^+$: m/z=339.1. found: 339.0.

Step 6. 8-(3,5-Dimethylisoxazol-4-yl)-6-fluoro-3-pyridin-3-yl-3,4-dihydro-2H-1,4-benzoxazin-5-amine

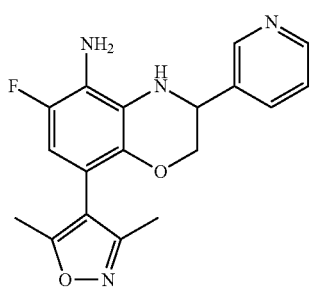 [SMILES: Cc1noc(C)c1-c1cc(F)c(N)c2c1OCC(c1cccnc1)N2]

To a solution of 8-(3,5-dimethylisoxazol-4-yl)-6-fluoro-3-pyridin-3-yl-2H-1,4-benzoxazin-5-amine (40 mg, 0.1 mmol) in ethanol (0.8 mL) and water (0.2 mL), sodium tetrahydroborate (4.5 mg, 0.12 mmol) was added and the mixture was heated at 90° C. for 15 minutes. Sodium tetrahydroborate (4.5 mg, 0.12 mmol) was added and the mixture was heated to 90° C. for 15 minutes again. The mixture was evaporated and extracted with ethyl acetate. The organic extracts were evaporated. Purification by preparative LCMS (pH 10) gave the desired compound 11 mg, 30%. $^1$H NMR (300 MHz, DMSO-$d_6$) δ 8.62 (s, 1H), 8.50 (m, 1H), 7.80 (m, 1H), 7.40 (m, 1H), 6.35 (m, 1H), 5.61 (s, 1H), 4.78 (s, 2H), 4.60 (m, 1H), 4.20 (m, 1H), 3.98 (m, 1H), 2.20 (s, 3H), 2.01 (s, 3H). LCMS calculated for $C_{18}H_{18}FN_4O_2$ $(M+H)^+$: m/z=341.1. found: 340.9.

Step 7. 7-(3,5-Dimethylisoxazol-4-yl)-9-fluoro-4-pyridin-3-yl-4,5-dihydro[1,2,3]triazolo[1,5,4-de][1,4]benzoxazine trifluoroacetate To a solution of 8-(3,5-dimethylisoxazol-4-yl)-6-fluoro-3-pyridin-3-yl-3,4-dihydro-2H-1,4-benzoxazin-5-amine (9.0 mg, 0.026 mmol) in 5.0 M hydrogen chloride in water (0.26 mL, 1.3 mmol) at 0° C., was added a solution of sodium nitrite (3.6 mg, 0.053 mmol) in water (100 µL). The reaction mixture was stirred at 0° C. for 10 min and at RT for 20 minutes. Purification by preparative LCMS (pH 2) gave the desired compound, 7 mg, 60%. $^1$H NMR (300 MHz, DMSO-$d_6$) δ 8.62 (m, 2H), 7.79 (m, 1H), 7.50 (m, 1H), 7.29 (m, 1H), 6.41 (m, 1H), 4.92 (m, 1H), 4.79 (m, 1H), 2.37 (s, 3H), 2.20 (s, 3H). LCMS calculated for $C_{18}H_{15}FN_5O_2$ $(M+H)^+$: m/z=352.1. found: 351.9.

Biological Assay Protocols

Example Assay A1

BRD4 AlphaScreen™ Assay

BRD4-BD1 and BRD4-BD2 assays were conducted in white 384-well polystyrene plate in a final volume of 20 µL for BD1 and 40 µL for BD2. Inhibitors were first serially diluted in DMSO and added to the plate wells before the addition of other reaction components. The final concentration of DMSO in the assay was 1.25% (BD1) and 0.83% (BD2). The assays were carried out at room temperature for 75 min. in the assay buffer (50 mM HEPES, pH 7.4, 100 mM NaCl, 0.05% CHAPS, 0.01% BSA), containing 50 nM Biotin-labeled tetra-acetylated histone H4 peptide (H4Ac4), 3.8 nM (BRD4-BD1, BPS Bioscience #31040) or 20 nM (BRD4-BD2, BPS Bioscience #31041). The reaction followed by the addition of 20 µL of assay buffer supplemented with Streptavidin donor beads (PerkinElmer 6760002) and GSH Acceptor beads (PerkinElmer-AL109C) at 4 µg/mL under reduced light. After plate sealing, the plate was incubated in the dark at room temperature for 75 min. before reading on a PHERAstar FS plate reader (BMG Labtech). $IC_{50}$ determination was performed by fitting the curve of percent control activity versus the log of the inhibitor concentration using the GraphPad Prism 5.0 software.

$IC_{50}$ data for the compounds of the Examples as determined by Assay A1 is presented in Table 1.

TABLE 1

| Example No. | BRD4 BD-1 enzyme $IC_{50}$ (nM)* | BRD4 BD-2 enzyme $IC_{50}$ (nM)* |
|---|---|---|
| 1 | + | + |
| 2 | + | + |
| 3 | + | + |
| 4 | + | + |
| 5 | ++ | + |

TABLE 1-continued

| Example No. | BRD4 BD-1 enzyme IC$_{50}$ (nM)* | BRD4 BD-2 enzyme IC$_{50}$ (nM)* |
|---|---|---|
| 6 | + | + |
| 7 | + | + |
| 8 | + | + |
| 9 | ++ | + |
| 10 | ++ | + |
| 11 | + | + |
| 12 | + | + |
| 13 | +++ | ++ |

*Symbols used: +: IC$_{50}$ ≤ 200 nM ++: 200 nM < IC$_{50}$ ≤ 1000 nM +++: IC$_{50}$ > 1000 nM Example Assay B1

KMS.12.BM Cell Viability Assay

KMS.12.BM cell line (human myeloma) was purchased from JCRB (Osaka, Japan) and maintained in RPMI with 10% FBS culture medium. To measure the cytotoxic activity of the compounds through ATP quantitation, the KMS.12.BM cells are plated in the RPMI culture medium at 5000 cells/well/per 100 µL into a 96-well polystyrene clear black tissue culture plate (Greiner-bio-one through VWR, NJ), in the presence or absence of a concentration range of test compounds. After 3 days, 100 mL Cell Titer-GLO Luminescent (Promega, Madison, Wis.) cell culture agent is added to each well for 10 minutes at room temperature to stabilize the luminescent signal. This determines the number of viable cells in culture based on quantitation of the ATP present, which signals the presence of metabolically active cells. Luminescence is measured with the Top Count 384 (Packard Bioscience through Perkin Elmer, Boston, Mass.). Compound inhibition is determined relative to cells cultured with no drug and the IC$_{50}$ reported as the compound concentration required for 50% cell death.

IC$_{50}$ data for the compounds of the Examples as determined by Assay B1 is presented in Table 2.

TABLE 2

| Example No. | KMS cellular IC$_{50}$ (nM)* |
|---|---|
| 1 | + |
| 2 | + |
| 3 | + |
| 4 | + |
| 5 | + |
| 6 | + |
| 7 | + |
| 8 | + |
| 9 | ++ |
| 10 | ++ |
| 11 | + |
| 12 | + |
| 13 | NA |

*Symbols used: +: IC$_{50}$ ≤ 1000 nM ++: 1000 nM < IC$_{50}$ ≤ 10000 nM NA: Not available Example Assay C1

KMS.12.BM C-Myc ELISA Assay

KMS.12.BM cell line (human myeloma) was purchased from JCRB (Osaka, Japan) and maintained in RPMI with 10% FBS culture medium. To measure the C-myc inhibitory activity of the compounds, the KMS.12.BM cells are plated in the RPMI culture medium at 75000 cells/well/per 200 µL into a 96-well flat bottom polystyrene tissue culture plate (Corning through VWR, NJ), in the presence or absence of a concentration range of test compounds. After 2 hours, cell are pelleted and lysed with Cell Extraction Buffer (BioSource, Carlsbad, Calif.) in the presence of protease inhibitors (Lifetechnologies, Grand Island, N.Y. and Sigma, St Louis, Mo.). Clarified lyses are tested in a C-myc commercial ELISA (Lifetechnologies, Grand Island, N.Y.). Compound inhibition is determined relative to cells cultured with no drug and the IC$_{50}$ reported as the compound concentration required for 50% C-myc inhibition Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula (I):

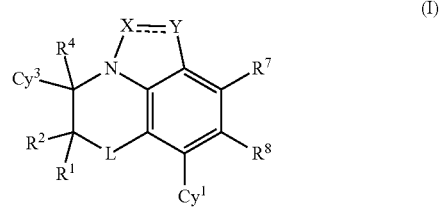

(I)

or a pharmaceutically acceptable salt thereof, wherein:

represents a single bond or a double bond;

L is O;

X is N or NR$^5$;

Y is N, CR$^6$, C(=O), or C(=S);

provided X is not NR$^5$ when Y is N;

Cy$^1$ is selected from phenyl and a 5-6 membered heteroaryl group comprising carbon and 1, 2, 3 or 4 heteroatoms selected from N, O and S, wherein said phenyl and 5-6 membered heteroaryl of Cy$^1$ are optionally substituted with 1, 2, 3, or 4 groups independently selected from R$^{11}$;

R$^1$ and R$^2$ are independently selected from H, halo, CN, OH, C$_{1-6}$ alkyl, C$_{2-6}$ alkenyl, C$_{2-6}$ alkynyl, C$_{1-6}$ haloalkyl, OR$^{a1}$, SR$^{a1}$, C(=O)R$^{b1}$, C(=O)NR$^{c1}$R$^{d1}$, C(=O)OR$^{a1}$, OC(=O)R$^{b1}$, OC(=O)NR$^{c1}$R$^{d1}$, NR$^{c1}$R$^{d1}$, NR$^{c1}$C(=O)R$^{b1}$, NR$^{c1}$C(=O)NR$^{c1}$R$^{d1}$, NR$^{c1}$C(=O)OR$^{a1}$, S(=O)R$^{b1}$, S(=O)NR$^{c1}$R$^{d1}$, S(=O)$_2$R$^{b1}$, NR$^{c1}$S(=O)$_2$R$^{b1}$ and S(=O)$_2$NR$^{c1}$R$^{d1}$, wherein said C$_{1-6}$ alkyl, C$_{2-6}$ alkenyl, and C$_{2-6}$ alkynyl of R$^1$ and R$^2$ are optionally substituted with 1, 2, or 3 groups independently selected from halo, CN, OH, OR$^{a1}$, SR$^{a1}$, C(=O)R$^{b1}$, C(=O)NR$^{c1}$R$^{d1}$, C(=O)OR$^{a1}$, OC(=O)R$^{b1}$, OC(=O)NR$^{c1}$R$^{d1}$, NR$^{c1}$R$^{d1}$, NR$^{c1}$C(=O)R$^{b1}$, NR$^{c1}$C(=O)NR$^{c1}$R$^{d1}$, NR$^{c1}$C(=O)OR$^{a1}$, S(=O)R$^{b1}$, S(=O)NR$^{c1}$R$^{d1}$, S(=O)$_2$R$^{b1}$, NR$^{c1}$S(=O)$_2$R$^{b1}$ and S(=O)$_2$NR$^{c1}$R$^{d1}$;

provided R$^1$ and R$^2$ are other than Cl, Br, I, CN, and OH when L is O;

alternatively, R$^1$ and R$^2$ together with the carbon atom to which they are attached form a C$_{3-7}$ cycloalkyl group, wherein said cycloalkyl group is optionally substituted with 1, 2, 3, or 4 groups independently selected from R$^{20}$;

Cy³ is selected from phenyl, $C_{3-7}$ cycloalkyl, a 5-10 membered heteroaryl group comprising carbon and 1, 2, 3 or 4 heteroatoms selected from N, O and S, and a 4-10 membered heterocycloalkyl group comprising carbon and 1, 2, or 3 heteroatoms selected from N, O and S, wherein said phenyl, $C_{3-7}$ cycloalkyl, 5-10 membered heteroaryl, and 4-10 membered heterocycloalkyl of Cy³ are optionally substituted with 1, 2, 3, or 4 groups independently selected from $R^{13}$, wherein a ring-forming nitrogen atom of said 5-10 membered heteroaryl group or a ring-forming nitrogen atom of said 4-10 membered heterocycloalkyl group is optionally oxidized;

$R^4$ is H or $C_{1-6}$ alkyl;

$R^5$ is selected from H, $C_{1-6}$ alkyl, $C_{2-6}$ alkenyl, $C_{2-6}$ alkynyl, $C_{1-6}$ haloalkyl, phenyl, $C_{3-7}$ cycloalkyl, a 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{1-6}$ alkyl, phenyl, $C_{3-7}$ cycloalkyl, 5-6 membered heteroaryl, and 4-7 membered heterocycloalkyl of $R^5$ are optionally substituted by 1, 2, 3, or 4 groups independently selected from $R^{15}$;

$R^6$ is selected from H, halo, CN, OH, $OR^{a6}$, $SR^{a6}$, $C(=O)R^{b6}$, $C(=O)NR^{c6}R^{d6}$, $C(=O)OR^{a6}$, $OC(=O)R^{b6}$, $OC(=O)NR^{c6}R^{d6}$, $NR^{c6}R^{d6}$, $NR^{c6}C(=O)R^{b6}$, $NR^{c6}R^{d6}$, $NR^{c6}C(=O)OR^{a6}$, $S(=O)R^{b6}$, $S(=O)NR^{c6}R^{d6}$, $S(=O)_2R^{b6}$, $NR^{c6}S(=O)_2R^{b6}$, $S(=O)_2NR^{c6}R^{d6}$, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, $C_{2-6}$ alkynyl of $R^6$ are each optionally substituted by 1, 2, 3, or 4 groups independently selected from $R^{16}$;

alternatively, $R^6$ is selected from $C_{6-10}$ aryl, $C_{3-7}$ cycloalkyl, a 5-10 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{6-10}$ aryl, $C_{3-7}$ cycloalkyl, 5-10 membered heteroaryl, and 4-7 membered heterocycloalkyl of $R^6$ are each optionally substituted by 1, 2, 3, or 4 groups independently selected from $R^{20}$;

$R^7$ is selected from H, halo, CN, $OR^a$, $NR^cR^d$, $SR^b$, $CONR^cR^d$, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{1-6}$ alkyl, $C_{2-6}$ alkenyl, $C_{2-6}$ alkynyl, phenyl, $C_{3-7}$ cycloalkyl, 5-6 membered heteroaryl group, and 4-7 membered heterocycloalkyl group of $R^7$ are optionally substituted with 1, 2, or 3 groups independently selected from $R^{17}$;

$R^8$ is selected from H, $C_{1-3}$ alkyl, $C_{2-3}$ alkenyl, $C_{2-3}$ alkynyl, $C_{1-3}$ haloalkyl, halo, CN, $OR^a$, $NR^cR^d$, $SR^b$, and $CONR^cR^d$, wherein said $C_{1-3}$ alkyl, $C_{2-3}$ alkenyl, and $C_{2-3}$ alkynyl of $R^8$ are optionally substituted with 1, 2, or 3 groups independently selected from $R^{18}$;

$R^{11}$ is independently at each occurrence selected from H, $C_{1-3}$ alkyl, $C_{1-3}$ haloalkyl, halo, CN, $OR^a$, $NR^cR^d$, $SR^b$, and $CONR^cR^d$;

$R^{13}$ is independently at each occurrence selected from H, halo, CN, OH, $C_{1-6}$ alkyl, $C_{2-6}$ alkenyl, $C_{2-6}$ alkynyl, $C_{1-6}$ haloalkyl, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $S(=O)R^{b3}$, $S(=O)NR^{c3}R^{d3}$, $S(=O)_2R^{b3}$, $NR^{c3}S(=O)_2R^{b3}$ and $S(=O)_2NR^{c3}R^{d3}$, wherein said $C_{1-6}$ alkyl, $C_{2-6}$ alkenyl, and $C_{2-6}$ alkynyl of $R^{13}$ are optionally substituted with 1, 2, or 3 groups independently selected from halo, CN, OH, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)NR^{c3}R^{d3}$, $NR^{c3}C(=O)OR^{a3}$, $S(=O)R^{b3}$, $S(=O)NR^{c3}R^{d3}$, $S(=O)_2R^{b3}$, $NR^{c3}S(=O)_2R^{b3}$ and $S(=O)_2NR^3R^{d3}$;

$R^{15}$ is independently at each occurrence selected from H, halo, CN, OH, $C_{1-6}$ alkyl, $C_{2-6}$ alkenyl, $C_{2-6}$ alkynyl, $C_{1-6}$ haloalkyl, $OR^{a5}$, $SR^{a5}$, $C(=O)R^{b5}$, $C(=O)NR^{c5}R^{c5}$, $C(=O)OR^{a5}$, $OC(=O)R^{b5}$, $OC(=O)NR^{c5}R^{c5}$, $NR^{c5}R^{c5}$, $NR^{c5}C(=O)R^{b5}$, $NR^{c5}C(=O)NR^{c5}R^{c5}$, $NR^{c5}C(=O)OR^{a5}$, $S(=O)R^{b5}$, $S(=O)NR^{c5}R^{c5}$, $S(=O)_2R^{b5}$, $NR^{c5}S(=O)_2R^{b5}$ and $S(=O)_2NR^{c5}R^{d5}$, wherein said $C_{1-6}$ alkyl, $C_{2-6}$ alkenyl, and $C_{2-6}$ alkynyl of $R^{15}$ are optionally substituted with 1, 2, or 3 groups independently selected from halo, CN, OH, $OR^{a5}$, $SR^{a5}$, $C(=O)R^{b5}$, $C(=O)NR^{c5}R^{c5}$, $C(=O)OR^{a5}$, $OC(=O)R^{b5}$, $OC(=O)NR^{c5}R^{c5}$, $NR^{c5}R^{c5}$, $NR^{c5}C(=O)R^{b5}$, $NR^{c5}C(=O)NR^{c5}R^{c5}$, $NR^{c5}C(=O)OR^{a5}$, $S(=O)R^{b5}$, $S(=O)NR^{c5}R^{c5}$, $S(=O)_2R^{b5}$, $NR^{c5}S(=O)_2R^{b5}$ and $S(=O)_2NR^{c5}R^{d5}$;

$R^{16}$ is independently at each occurrence selected from halo, CN, OH, $OR^{a6}$, $SR^{a6}$, $C(=O)R^{b6}$, $C(=O)NR^{c6}R^{d6}$, $C(=O)OR^{a6}$, $OC(=O)R^{b6}$, $OC(=O)NR^{c6}R^{d6}$, $NR^{c6}R^{d6}$, $NR^{c6}C(=O)R^{b6}$, $NR^{c6}C(=O)NR^{c6}R^{d6}$, $NR^{c6}C(=O)OR^{a6}$, $S(=O)R^{b6}$, $S(=O)NR^{c6}R^{d6}$, $S(=O)_2R^{b6}$, $NR^{c6}S(=O)_2R^{b6}$, $S(=O)_2NR^{c6}R^{d6}$, $C_{6-10}$ aryl, $C_{3-7}$ cycloalkyl, a 5-10 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{6-10}$ aryl, $C_{3-7}$ cycloalkyl, 5-10 membered heteroaryl, and 4-7 membered heterocycloalkyl of $R^{16}$ are each optionally substituted by 1, 2, 3, or 4 groups independently selected $R^{20}$;

$R^{17}$ and $R^{18}$ are independently at each occurrence selected from halo, CN, OH, $OR^a$, $NR^cR^d$, $SR^b$, and $CONR^cR^d$;

$R^a$, $R^c$, and $R^d$ are independently at each occurrence selected from H and $C_{1-6}$ alkyl;

$R^b$ is at each occurrence $C_{1-6}$ alkyl;

$R^{a1}$, $R^{b1}$, $R^{c1}$ and a $R^{d1}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a1}$, $R^{b1}$, $R^{c1}$ and $R^{d1}$ are each optionally substituted with 1, 2, or 3 substituents independently selected from $R^{20}$;

$R^{a3}$, $R^{b3}$, $R^{a1}$ and $R^{d3}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a3}$, $R^{b3}$, $R^{a1}$ and $R^{d3}$ are each optionally substituted with 1, 2, or 3 substituents independently selected from halo, CN, OH, OR', SR', $C(=O)R^{b4}$, $C(=O)NR^{11}R^{11}$, $C(=O)OR^{a4}$, $OC(=O)R^{b4}$, $OC(=O)NR^{11}R^{11}$, $NR^{11}R^{11}$, $NR^{11}C(=O)R^{b4}$, $NR^{11}C(=O)NR^{11}R^{11}$, $NR^{11}C(=O)OR^{a4}$, $S(=O)R^{b4}$, $S(=O)NR^{c4}R^{d4}$, $S(=O)_2R^{b4}$, $NR^{c4}S(=O)_2R^{b4}$ and $S(=O)_2NR^{c4}R^{d4}$;

$R^{a4}$, $R^{b4}$, $R^{c4}$ and $R^{d4}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a4}$, $R^{b4}$, $R^{c4}$ and $R^{d4}$ are each optionally substituted with 1, 2, or 3 substituents independently selected from $R^{20}$;

$R^{a5}$, $R^{b5}$, $R^{c5}$ and $R^{d5}$ are independently at each occurrence selected from H, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, and $C_{2-6}$ alkynyl forming $R^{a5}$, $R^{b5}$, $R^{c5}$ and $R^{d5}$ are each optionally substituted with 1, 2, or 3 substituents independently selected from $R^{20}$;

$R^{a6}$, $R^{c6}$ and $R^{d6}$ are independently at each occurrence selected from H, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl group, and 4-7 membered heterocycloalkyl group forming $R^{a6}$, $R^{c6}$ and $R^{d6}$ are each optionally substituted with 1, 2, or 3 substituents independently selected from $R^{20}$;

alternatively, $R^{c6}$ and $R^{d6}$ together with the nitrogen atom to which they are attached may be combined to form a 4-7 membered heterocycloalkyl group comprising carbon, nitrogen, and 0, 1, or 2 additional heteroatoms selected from N, O and S, wherein said 4-7 membered heterocycloalkyl group is optionally substituted with 1, 2, or 3 substituents independently selected from $R^{20}$;

$R^{b6}$ is independently at each occurrence selected from $C_{1-6}$ alkyl, $C_{2-6}$ alkenyl, $C_{2-6}$ alkynyl, $C_{1-6}$ haloalkyl, phenyl, $C_{3-7}$ cycloalkyl, a 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl group, and 4-7 membered heterocycloalkyl group are each optionally substituted with 1, 2, or 3 substituents independently selected from $R^{20}$; and $R^{20}$ is at each occurrence independently selected from H, halo, OH, CN, amino, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ halo alkyl, $C_{1-4}$ haloalkoxy, $C_{1-4}$ alkyl-C(=O)—, $C_{1-4}$ alkyl-C(=O)O—, $C_{1-4}$ alkyl-OC(=O)—, HOC(=O)—, $H_2NC(=O)$—, $C_{1-4}$ alkyl-NHC(=O)—, di($C_{1-4}$ alkyl)NC(=O)—, $C_{1-4}$ alkyl-C(=O)NH—, $C_{1-4}$ alkyl-S(=O)—, $H_2NS(=O)$—, $C_{1-4}$ alkyl-NHS(=O)—, di($C_{1-4}$ alkyl)NS(=O)—, $C_{1-4}$ alkyl-S(=O)$_2$—, $C_{1-4}$ alkyl-S(=O)$_2$NH—, $H_2NS(=O)_2$—, $C_{1-4}$ alkyl-NHS(=O)$_2$—, and di($C_{1-4}$ alkyl)NS(=O)$_2$—.

2. The compound of claim 1, or a pharmaceutically acceptable salt thereof, wherein X is N.

3. The compound of claim 1, or a pharmaceutically acceptable salt thereof, wherein X is $NR^5$.

4. The compound of claim 1, or a pharmaceutically acceptable salt thereof, wherein Y is $CR^6$.

5. The compound of claim 1, or a pharmaceutically acceptable salt thereof, wherein Y is C(=O).

6. The compound of claim 1, or a pharmaceutically acceptable salt thereof, wherein X==Y is N=N.

7. The compound of claim 1, or a pharmaceutically acceptable salt thereof, wherein $Cy^1$ is isoxazolyl substituted with 1 or 2 groups independently selected from $R^{11}$.

8. The compound of claim 1, or a pharmaceutically acceptable salt thereof, wherein $Cy^1$ is pyrazolyl substituted with 1 or 2 groups independently selected from $R^{11}$.

9. The compound of claim 1, or a pharmaceutically acceptable salt thereof, wherein $R^1$ is selected from H, methyl, —C(=O)OCH$_2$CH$_3$, —C(=O)N(H)CH$_2$CH$_3$, —C(=O)N(H)CH$_2$CH$_2$OH, and —C(=O)N(CH$_3$)$_2$.

10. The compound of claim 1, or a pharmaceutically acceptable salt thereof, wherein $R^1$ is H.

11. The compound of claim 1, or a pharmaceutically acceptable salt thereof, wherein $R^1$ is methyl.

12. The compound of claim 1, or a pharmaceutically acceptable salt thereof, wherein $R^2$ is H.

13. The compound of claim 1, or a pharmaceutically acceptable salt thereof, wherein $Cy^3$ is selected from phenyl, pyridinyl, oxidopyridinyl, thiazolyl, cyclohexyl, dihydrobenzofuranyl and tetrahydrofuranyl, wherein said phenyl, pyridinyl, oxidopyridinyl, thiazolyl, cyclohexyl, dihydrobenzofuranyl and tetrahydrofuranyl is optionally substituted with 1, 2, 3, or 4 groups independently selected from $R^{13}$.

14. The compound of claim 1, or a pharmaceutically acceptable salt thereof, wherein $Cy^3$ is phenyl optionally substituted with 1, 2, 3, or 4 groups independently selected from $R^{13}$.

15. The compound of claim 1, or a pharmaceutically acceptable salt thereof, wherein $Cy^3$ is pyridinyl optionally substituted with 1, 2, 3, or 4 groups independently selected from $R^{13}$.

16. The compound of claim 1, or a pharmaceutically acceptable salt thereof, wherein $Cy^3$ is oxidopyridinyl optionally substituted with 1, 2, 3, or 4 groups independently selected from $R^{13}$.

17. The compound of claim 1, or a pharmaceutically acceptable salt thereof, wherein $Cy^3$ is thiazolyl optionally substituted with 1, 2, 3, or 4 groups independently selected from $R^{13}$.

18. The compound of claim 1, or a pharmaceutically acceptable salt thereof, wherein $Cy^3$ is cyclohexyl optionally substituted with 1, 2, 3, or 4 groups independently selected from $R^{13}$.

19. The compound of claim 1, or a pharmaceutically acceptable salt thereof, wherein $Cy^3$ is dihydrobenzofuranyl optionally substituted with 1, 2, 3, or 4 groups independently selected from $R^{13}$.

20. The compound of claim 1, or a pharmaceutically acceptable salt thereof, wherein $Cy^3$ is tetrahydrofuranyl optionally substituted with 1, 2, 3, or 4 groups independently selected from $R^{13}$.

21. The compound of claim 1, or a pharmaceutically acceptable salt thereof, wherein $R^5$ is methyl.

22. The compound of claim 1, or a pharmaceutically acceptable salt thereof, wherein $R^5$ is H.

23. The compound of claim 1, or a pharmaceutically acceptable salt thereof, wherein $R^6$ is H, $C_{1-6}$ alkoxy, $C_{1-6}$ alkyl, $C_{2-6}$ alkenyl, $C_{2-6}$ alkynyl, or $C_{1-6}$ haloalkyl.

24. The compound of claim 1, or a pharmaceutically acceptable salt thereof, wherein $R^6$ is H.

25. The compound of claim 1, or a pharmaceutically acceptable salt thereof, wherein $R^6$ is methoxy.

26. The compound of claim 1, or a pharmaceutically acceptable salt thereof, wherein $R^7$ is selected from H, halo, $C_{1-4}$ alkyl, and CN.

27. The compound of claim 1, or a pharmaceutically acceptable salt thereof, wherein $R^7$ is selected from H, Br, F, methyl, and CN.

28. The compound of claim 1, or a pharmaceutically acceptable salt thereof, wherein $R^7$ is H.

29. The compound of claim 1, or a pharmaceutically acceptable salt thereof, wherein $R^7$ is Br.

30. The compound of claim 1, or a pharmaceutically acceptable salt thereof, wherein $R^7$ is F.

31. The compound of claim 1, or a pharmaceutically acceptable salt thereof, wherein $R^7$ is methyl.

32. The compound of claim 1, or a pharmaceutically acceptable salt thereof, wherein $R^7$ is CN.

33. The compound of claim 1, or a pharmaceutically acceptable salt thereof, wherein $R^8$ is selected from H, halo, $C_{1-4}$ alkyl, and CN.

34. The compound of claim 1, or a pharmaceutically acceptable salt thereof, wherein $R^8$ is H.

35. The compound of claim 1 having Formula (IIa), (IIb), or (IIc):

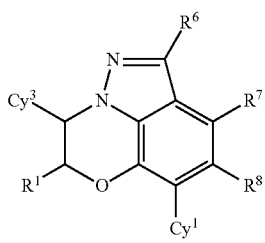
(IIa)

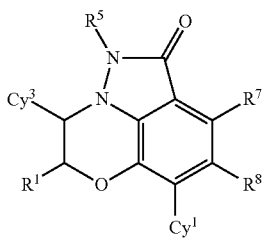
(IIb)

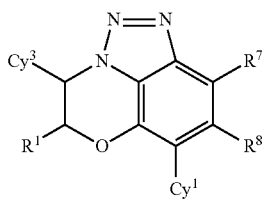
(IIc)

or a pharmaceutically acceptable salt thereof.

36. The compound of claim 1, having Formula (IIIa), (IIIb), or (IIIc):

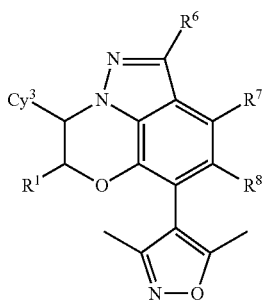
(IIIa)

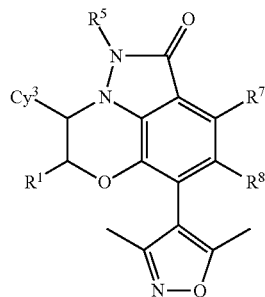
(IIIb)

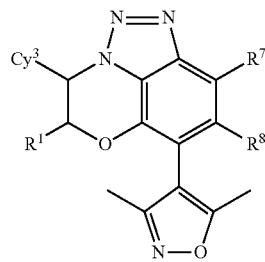
(IIIc)

or a pharmaceutically acceptable salt thereof.

37. The compound of claim 1, or a pharmaceutically acceptable salt thereof, wherein:
L is O;
Y is N, $CR^6$, or C(=O);
$Cy^1$ is a 5-6 membered heteroaryl group comprising carbon and 1, 2, 3 or 4 heteroatoms selected from N, O and S, wherein said 5-6 membered heteroaryl of $Cy^1$ is optionally substituted with 1, 2, 3, or 4 groups independently selected from $R^{11}$;
$R^1$ is selected from H, F, $C_{1-6}$ alkyl, $C_{2-6}$ alkenyl, $C_{2-6}$ alkynyl, $C_{1-6}$ haloalkyl, $C_{1-6}$ alkyl, $C_{2-6}$ alkenyl, and $C_{2-6}$ alkynyl of $R^1$ is optionally substituted with 1, 2, or 3 groups independently selected from halo, CN, OH, $OR^{a1}$, $C(=O)R^{b1}$, $C(=O)NR^{c1}R^{d1}$, $C(=O)OR^{a1}$, $NR^{c1}R^{d1}$, and $NR^{c1}C(=O)R^{b1}$; provided $R^1$ is not OH;
$R^7$ is selected from H, halo, CN, $OR^a$, $C_{1-6}$ alkyl, $C_{1-6}$ haloalkyl, phenyl, $C_{3-7}$ cycloalkyl, 5-6 membered heteroaryl group comprising carbon and 1, 2, 3 or 4 heteroatoms selected from N, O and S, and a 4-7 membered heterocycloalkyl group comprising carbon and 1, 2, or 3 heteroatoms selected from N, O and S, wherein said $C_{1-6}$ alkyl, phenyl, $C_{3-7}$ cycloalkyl, 5-6 membered heteroaryl group, and 4-7 membered heterocycloalkyl group of $R^7$ are optionally substituted with 1, 2, or 3 groups independently selected from $R^{17}$;
$R^8$ is selected from H and $C_{1-3}$ alkyl; and
$R^{a1}$, $R^{b1}$, $R^{c1}$ and $R^{d1}$ are independently at each occurrence selected from H, $C_{1-6}$ alkyl, and $C_{1-6}$ haloalkyl.

38. The compound of claim 1, or a pharmaceutically acceptable salt thereof, wherein:
L is O;
Y is N, $CR^6$, or C(=O);
$Cy^1$ is a 5-membered heteroaryl group comprising carbon and 1, 2, 3 or 4 heteroatoms selected from N, O and S, wherein said 5-membered heteroaryl of $Cy^1$ is optionally substituted with 1, 2, 3, or 4 groups independently selected from $R^{11}$;
$R^1$ and $R^2$ are both H;
$Cy^3$ is selected from phenyl and a 5-6 membered heteroaryl group comprising carbon and 1, 2, 3 or 4 heteroatoms selected from N, O and S, wherein said phenyl and 5-6 membered heteroaryl of $Cy^3$ are optionally substituted with 1, 2, 3, or 4 groups independently selected from $R^{13}$, wherein a ring-forming nitrogen atom of said 5-6 membered heteroaryl group;

$R^4$ is H;
$R^5$ is selected from H and $C_{1-6}$ alkyl;
$R^6$ is selected from H, $OR^{a6}$;
$R^7$ is selected from H and halo; and
$R^8$ is H.

39. The compound of claim 1 selected from:
9-(3,5-dimethylisoxazol-4-yl)-3-phenyl-2,3-dihydro[1,4]oxazino[2,3,4-hi]indazol-6(5H)-one;
9-(3,5-dimethylisoxazol-4-yl)-5-methyl-3-phenyl-2,3-dihydro[1,4]oxazino[2,3,4-hi]indazol-6(5H)-one;
9-(3,5-dimethylisoxazol-4-yl)-6-methoxy-3-phenyl-2,3-dihydro[1,4]oxazino[2,3,4-hi]indazole;
9-(3,5-dimethylisoxazol-4-yl)-3-phenyl-2,3-dihydro[1,4]oxazino[2,3,4-hi]indazole;
9-(3,5-dimethylisoxazol-4-yl)-3-pyridin-2-yl-2,3-dihydro[1,4]oxazino[2,3,4-hi]indazol-6(5H)-one;
9-(3,5-dimethylisoxazol-4-yl)-5-methyl-3-pyridin-2-yl-2,3-dihydro[1,4]oxazino[2,3,4-hi]indazol-6(5H)-one;
9-(3,5-dimethylisoxazol-4-yl)-6-methoxy-3-pyridin-2-yl-2,3-dihydro[1,4]oxazino[2,3,4-hi]indazole;
9-(3,5-dimethylisoxazol-4-yl)-3-pyridin-2-yl-2,3-dihydro[1,4]oxazino[2,3,4-hi]indazole;
7-bromo-9-(3,5-dimethylisoxazol-4-yl)-3-phenyl-2,3-dihydro[1,4]oxazino[2,3,4-hi]indazole;
9-(3,5-dimethylisoxazol-4-yl)-3-pyridin-3-yl-2,3-dihydro[1,4]oxazino[2,3,4-hi]indazol-6(5H)-one;
9-(3,5-dimethylisoxazol-4-yl)-5-methyl-3-pyridin-3-yl-2,3-dihydro[1,4]oxazino[2,3,4-hi]indazol-6(5H)-one;
9-(3,5-dimethylisoxazol-4-yl)-6-methoxy-3-pyridin-3-yl-2,3-dihydro[1,4]oxazino[2,3,4-hi]indazole; and
7-(3,5-dimethylisoxazol-4-yl)-9-fluoro-4-pyridin-3-yl-4,5-dihydro[1,2,3]triazolo[1,5,4-de][1,4]benzoxazine;
or a pharmaceutically acceptable salt of any of the aforementioned.

40. A pharmaceutical composition comprising a compound of claim 1, or a pharmaceutically acceptable salt thereof, and at least one pharmaceutically acceptable carrier.

41. A method of treating cancer comprising administering to a patient in need of such treatment a therapeutically effective amount of a compound of claim 1, wherein the cancer is adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor.

42. A method of treating an autoimmune or inflammatory disease comprising administering to a patient in need of such treatment a therapeutically effective amount of claim 1, wherein the autoimmune or inflammatory disease is selected from allergy, allergic rhinitis, arthritis, asthma, chronic obstructive pulmonary disease, degenerative joint disease, dermatitis, organ rejection, eczema, hepatitis, inflammatory bowel disease, multiple sclerosis, myasthenia gravis, psoriasis, sepsis, sepsis syndrome, septic shock, systemic lupus erythematosus, tissue graft rejection, type I diabetes.

43. A method of treating a viral infection comprising administering to a patient in need of such treatment a therapeutically effective amount of a compound of claim 1, or a pharmaceutically acceptable salt thereof.

44. The method of claim 43, wherein the viral infection is infection with adenovirus, Epstein-Barr virus, hepatitis B virus, hepatitis C virus, a herpes virus, human immunodeficiency virus, human papilloma virus or a pox virus.

* * * * *